US012606613B2

(12) United States Patent
Guo et al.

(10) Patent No.: US 12,606,613 B2
(45) Date of Patent: Apr. 21, 2026

(54) HUMANIZED ANTI-C5a ANTIBODIES

(71) Applicant: InflaRx GmbH, Jena (DE)

(72) Inventors: Renfeng Guo, Ann Arbor, MI (US);
Niels C. Riedemann, Jena (DE)

(73) Assignee: InflaRx GmbH, Jena (DE)

( * ) Notice: Subject to any disclaimer, the term of this
patent is extended or adjusted under 35
U.S.C. 154(b) by 696 days.

(21) Appl. No.: 17/923,462

(22) PCT Filed: May 6, 2021

(86) PCT No.: PCT/EP2021/061940
§ 371 (c)(1),
(2) Date: Nov. 4, 2022

(87) PCT Pub. No.: WO2021/224366
PCT Pub. Date: Nov. 11, 2021

(65) Prior Publication Data
US 2023/0279087 A1       Sep. 7, 2023

(30) Foreign Application Priority Data

May 6, 2020   (EP) .................................... 20173255

(51) Int. Cl.
*C07K 16/18*       (2006.01)
*A61P 37/02*       (2006.01)

(52) U.S. Cl.
CPC .............. *C07K 16/18* (2013.01); *A61P 37/02*
(2018.01); *C07K 2317/24* (2013.01); *C07K
2317/565* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,704,355 A | 11/1987 | Bernstein | |
| 5,939,598 A | 8/1999 | Kucherlapati et al. | |
| 6,355,245 B1 | 3/2002 | Evans et al. | |
| 10,376,595 B2 | 8/2019 | Guo et al. | |
| 11,273,225 B2 | 3/2022 | Guo et al. | |
| 11,464,868 B2 | 10/2022 | Guo et al. | |
| 2003/0118592 A1 | 6/2003 | Ledbetter et al. | |
| 2003/0133939 A1 | 7/2003 | Ledbetter et al. | |
| 2004/0110226 A1 | 6/2004 | Lazar et al. | |
| 2010/0129346 A1 | 5/2010 | Mackay | |
| 2012/0219566 A1 | 8/2012 | Medof et al. | |
| 2012/0231008 A1 | 9/2012 | Guo et al. | |
| 2013/0004514 A1 | 1/2013 | Zahn et al. | |
| 2017/0137499 A1* | 5/2017 | Guo | A61P 31/12 |
| 2017/0349575 A1 | 12/2017 | Musicki et al. | |
| 2018/0280530 A1 | 10/2018 | Guo et al. | |
| 2018/0282425 A1 | 10/2018 | Guo et al. | |
| 2020/0061202 A1 | 2/2020 | Guo et al. | |
| 2020/0290969 A1 | 9/2020 | Li et al. | |
| 2021/0046191 A1 | 2/2021 | Guo et al. | |
| 2023/0158060 A1 | 5/2023 | Riedemann et al. | |
| 2024/0391995 A1* | 11/2024 | Riedemann | C07K 16/24 |

FOREIGN PATENT DOCUMENTS

| | | | |
|---|---|---|---|
| CN | 1604909 A | 4/2005 |
| CN | 1847261 A | 10/2006 |
| CN | 1997384 A | 7/2007 |
| CN | 105392803 A | 3/2016 |
| CN | 106132982 A | 11/2016 |
| CN | 111108118 A | 5/2020 |
| JP | 2012514465 A | 6/2012 |
| JP | 2014529997 A | 11/2014 |
| JP | 2015511965 A | 4/2015 |
| JP | 2016518331 A | 6/2016 |
| JP | 2016523829 A | 8/2016 |
| JP | 2017514791 A | 6/2017 |
| WO | 1991004014 A1 | 4/1991 |
| WO | 1999000406 A1 | 1/1999 |
| WO | 2001015731 A1 | 3/2001 |
| WO | 2003015819 A1 | 2/2003 |
| WO | 2003033528 A1 | 4/2003 |
| WO | 2005079363 A2 | 9/2005 |
| WO | 2005092366 A1 | 10/2005 |
| WO | 2006082406 A2 | 8/2006 |
| WO | 2008009062 A1 | 1/2008 |
| WO | 2008029167 A1 | 3/2008 |
| WO | 2010075257 A1 | 7/2010 |
| WO | 2010079314 A2 | 7/2010 |
| WO | 2011063980 A1 | 6/2011 |
| WO | 2011137395 A1 | 11/2011 |

(Continued)

OTHER PUBLICATIONS

Fireman B.V., inflaRx—Final Pursuant to 424(b)(a). pp. 1-229, Nov.
7, 2017 (Year: 2017).*
Inflarx—BDB contract. pp. 1-38, 2015. (Year: 2015).*
OfficeActiondatedNov. 11, 2025,incorrespondingKoreanPatentAp-
plicationNo. 10-2022-7033905(9pages). English Translation. (Year:
2025).*
Wang et al., "The role of C5a in acute lung injury induced by highly
pathogenic viral infections," Emerging Microbes & Infections,
2015, vol. 4, e28, pp. 1-7.
Weiss et al., "Rapid mapping of protein functional epitopes by
combinatorial alanine scanning," Proceedings of the National Acad-
emy of Sciences, Aug. 1, 2000, vol. 97, No. 16, pp. 8950-8954.

(Continued)

*Primary Examiner* — Maher M Haddad

(74) *Attorney, Agent, or Firm* — Greenberg Traurig, LLP;
Melissa Hunter-Ensor; Leslie Serunian

(57) ABSTRACT

The present invention relates to antibodies that specifically
bind to a conformational epitope of human C5a. The inven-
tion particularly relates to humanized anti-C5a antibodies.
The antibodies described herein are useful as active agents
in pharmaceutical compositions. The antibodies and phar-
maceutical compositions are especially useful for the treat-
ment and prevention of diseases or disorders involving
pathological C5a activity.

9 Claims, 3 Drawing Sheets

Specification includes a Sequence Listing.

(56) References Cited

FOREIGN PATENT DOCUMENTS

| WO | 2011163640 A1 | 12/2011 |
| WO | 2013041730 A1 | 3/2013 |
| WO | 2013138586 A1 | 9/2013 |
| WO | 2014160129 A2 | 10/2014 |
| WO | 2014180961 A1 | 11/2014 |
| WO | 2015140304 A1 | 9/2015 |
| WO | 2016044419 A1 | 3/2016 |
| WO | 2016061066 A1 | 4/2016 |
| WO | 2016102877 A1 | 6/2016 |
| WO | 2016209956 A1 | 12/2016 |
| WO | 2017176620 A2 | 10/2017 |
| WO | 2017218515 A1 | 12/2017 |
| WO | 2018175833 A1 | 9/2018 |
| WO | 2018184739 A1 | 10/2018 |
| WO | 2018234118 A1 | 12/2018 |
| WO | 2020051418 A1 | 3/2020 |
| WO | 2020182384 A1 | 9/2020 |
| WO | 2020214716 A1 | 10/2020 |
| WO | 2021188601 A1 | 9/2021 |
| WO | 2021190770 A1 | 9/2021 |
| WO | 2021205013 A1 | 10/2021 |
| WO | 2021211940 A1 | 10/2021 |

OTHER PUBLICATIONS

Werfel et al., "C5a receptors are detectable on mast cells in normal human skin and in psoriatic plaques but not in weal and flare reactions or in urticaria pigmentosa by immunohistochemistry," Archives of Dermatological Research, 1997, vol. 289, pp. 83-86.

Wills-Karp, Marsha, "Complement Activation Pathways: A Bridge between Innate and Adaptive Immune Responses in Asthma," Proceedings of the American Thoracic Society, 2007, vol. 4, pp. 247-251.

Wollina et al., "Acne inversa (Hidradenitis suppurativa): A review with a focus on pathogenesis and treatment," Indian Dermatology Online Journal, Jan.-Mar. 2013, vol. 4, No. 1, pp. 2-11.

Xu et al., "Complement C5a regulates IL-17 by affecting the crosstalk between DC and γδ T cells in CLP-induced sepsis," European Journal of Immunology, 2010, vol. 40, No. 4, pp. 1079-1088.

Zhang et al., "Antibody Responses Against SARS Coronavirus Are Correlated With Disease Outcome of Infected Individuals," Journal of Medical Virology, 2006, vol. 78, pp. 1-8.

Office Action dated Apr. 23, 2024 in corresponding Japanese Patent Application No. 2022-567241 (6 pages).

English translation of Office Action dated Apr. 23, 2024 in corresponding Japanese Patent Application No. 2022-567241 (5 pages).

Gueler et al., "Complement 5a Receptor Inhibition Improves Renal Allograft Survival," Journal of the American Society of Nephrology, 2008, vol. 19, pp. 2302-2312.

Guo et al., "Divergent Signaling Pathways in Phagocytic Cells during Sepsis," The Journal of Immunology, 2006, vol. 177, No. 2, pp. 1306-1313.

Guo et al., "IFX-1 blocking the anaphylatoxin C5a—an anti-inflammatory effect in patients with hidradenitis suppurativa," Aug. 29, 2017, poster (1 page).

Harding, J., "Eculizumab," Drugs of the Future, 2004, vol. 29, No. 7, pp. 673-676.

Höpken et al., "Inhibition of interleukin-6 synthesis in an animal model of septic shock by anti-C5a monoclonal antibodies," European Journal of Immunology, 1996, vol. 26, pp. 1103-1109.

Howard III et al., "Intracerebral drug delivery in rats with lesion-induced memory deficits," Journal of Neurosurgery, Jul. 1989, vol. 71, pp. 105-112.

Huber-Lang et al., "Protective effects of anti-C5a peptide antibodies in experimental sepsis," The FASEB Journal, Jan. 19, 2001, vol. 15, No. 3, pp. 568-570.

Hycult Biotech Catalog, "Complement and Collectins," 2020-2021, Uden, The Netherlands, pp. 1-8.

Hyzewicz et al., "Low-Intensity Training and the C5a Complement Antagonist NOX-D21 Rescue the mdx Phenotype through Modulation of Inflammation," The American Journal of Pathology, May 2017, vol. 187, No. 5, pp. 1147-1161.

Imagawa et al., "Consequences of cell membrane attack by complement: Release of arachidonate and formation of inflammatory derivatives," Proceedings of the National Academy of Sciences of the United States of America, Nov. 1983, vol. 80, pp. 6647-6651.

InflaRx, "InflaRx Reports Positive Results from the Open Label Extension Part of the SHINE Study for IFX-1 in Hidradenitis Suppurativa," Nov. 6, 2019, pp. 1-8.

InflaRx, "InflaRx initiates exploratory Phase II trial with IFX-1, a first-in-class anti-complement C5a antibody, in patients with Hidradenitis Suppurativa," Jan. 4, 2017, pp. 1-2.

InflaRx, "InflaRx Reports Additional Analysis of the SHINE Phase IIb Results for IFX-1 in Hidradenitis Suppurativa," Jul. 18, 2019, pp. 1-9.

Jayne et al., "Randomized Trial of C5a Receptor Inhibitor Avacopan in ANCA-Associated Vasculitis," Journal of the American Society of Nephrology, 2017, vol. 28, pp. 2756-2767.

Jemec et al., "The prevalence of hidradenitis suppurativa and its potential precursor lesions," Journal of the American Academy of Dermatology, Aug. 1996, vol. 35, No. 2, Pl. 1, pp. 191-194.

Jemec, Gregor B.E., "Medical treatment of hidradenitis suppurativa," Expert Opinion on Pharmacotherapy, 2004, vol. 5, No. 8, pp. 1767-1770.

Jiang et al., "Blockade of the C5a-C5aR axis alleviates lung damage in hDPP4-transgenic mice infected with MERS-CoV," Emerging Microbes & Infections, 2018, vol. 7, Article No. 77, pp. 1-12.

Jorizzo et al., "Low-dose weekly methotrexate for unusual neutrophilic vascular reactions: Cutaneous polyarteritis nodosa and Behçet's disease," Journal of the American Academy of Dermatology, Jun. 1991, vol. 24, No. 6, Pt. 1, pp. 973-978.

Kaplan, M., "Eculizumab," Current Opinion in Investigational Drugs, 2002, vol. 3, No. 7, pp. 1017-1023.

Kaplan, Mariana J., "Role of neutrophils in systemic autoimmune diseases," Arthritis Research & Therapy, 2013, vol. 15, Article No. 219, pp. 1-9.

Keseroglu et al., "A Case of Subcorneal Pustular Dermatosis Successfully Treated with Acitretin," Archives of Inflammation, Oct. 27, 2016, vol. 1, No. 2, pp. 1-3.

Khameneh et al., "C5a regulates IL-1β production and leukocyte recruitment in a murine model of monosodium urate crystal-induced peritonitis," Frontiers in Pharmacology, Jan. 23, 2017, vol. 8, Article 10, pp. 1-11.

Kimball et al., "Assessing the validity, responsiveness and meaningfulness of the Hidradenitis Suppurativa Clinical Response (HiSCR) as the clinical endpoint for hidradenitis suppurativa treatment," British Journal of Dermatology, 2014, vol. 171, No. 6, pp. 1434-1442.

Klos et al., "International Union of Basic and Clinical Pharmacology [corrected]. LXXXVII. Complement Peptide C5a, C4a, and C3a Receptors," Pharmacological Reviews, Jan. 2013, vol. 65, pp. 500-543.

Klos et al., "The role of the anaphylatoxins in health and disease," Molecular Immunology, 2009, vol. 46, pp. 2753-2766.

Kurzen et al., "What causes hidradenitis suppuraliva?" Experimental Dermatology, 2008, vol. 17, No. 5, pp. 455-456.

Kussie et al., "A Single Engineered Amino Acid Substitution Changes Antibody Fine Specificity," Journal of Immunology, 1994, vol. 152, pp. 146-152.

Langer et al., "Chemical and Physical Structure of Polymers as Carriers for Controlled Release of Bioactive Agents: A Review," Journal of Macromolecular Science, Reviews in Macromolecular Chemistry and Physics, 1983, vol. 23, No. 1, pp. 61-126.

Langer, Robert, "New Methods of Drug Delivery," Science, Sep. 28, 1990, vol. 249, pp. 1527-1533.

Li et al., "Melformin reduces diabetes-related inflammatory molecules in human vitreous and retinal vascular endolhelial cells," Investigative Ophthalmology & Visual Science, Sep. 2016, vol. 57, p. 6346; abstract submitted for the 2016 Annual Meeting of the Association for Research in Vision and Opthamology (ARVO).

(56) References Cited

OTHER PUBLICATIONS

Li et al., "Neuroprotective effects of argalroban and C5a receptor antagonist (PMX53) following intracerebral haemorrhage," Clinical and Experimental Immunology, 2014, vol. 175, No. 2, pp. 285-295.

Lima et al., "Keralinocytes and neutrophils are important sources of proinflammatory molecules in hidradenitis suppurativa," British Journal of Dermatology, 2016, vol. 174, pp. 514-521.

March et al., "Potent Cyclic Antagonists of the Complement C5a Receptor on Human Polymorphonuclear Leukocytes. Relationships between Structures and Activity," Molecular Pharmacology, 2004, vol. 65, No. 4, pp. 868-879.

Markiewski et al., "Modulation of the anti-tumor immune response by complement," Nature Immunology, Nov. 2008, vol. 9, No. 11, pp. 1225-1235.

Marzano et al., "Association of Pyodenrna Gangrenosum, Acne, and Suppurative Hidradenitis (PASH) Shares Genetic and Cytokine Profiles With Other Autoinflammatory Diseases," Medicine, Dec. 2014, vol. 93, No. 27, e187, pp. 1-11.

Marzano et al., "Hidradenitis suppurativa, neutrophilic denrnatoses and autoinflammation: what's the link?" British Journal of Dermatology, 2016, vol. 174, pp. 482-483.

Merle et al., "Complement System Part I—Molecular Mechanisms of Activation and Regulation," Frontiers in Immunology, Jun. 2, 2015, vol. 6, Article 262, pp. 1-30.

Morgan et al., "Complement, a target for therapy in inflammatory and degenerative diseases," Nature Reviews Drug Discovery, Dec. 2015, vol. 14, pp. 857-877.

Mourvillier et al., "LB1529. Randomized, Controlled Phase 3 Study of anti-C5a Vilobelimab's Effect on Mortality in Critically Ill COVID-19 Patients: A Therapy for Viral Pneumonia," Open Forum Infectious Diseases, Dec. 2022, vol. 9, Suppl. 2, p. S925.

Navarini et al., "Neutrophilic dermatoses and autoinflammatory diseases with skin involvement-innate immune disorders," Seminars in Immopathology, 2016, vol. 38, pp. 45-56.

Németh et al., "Neutrophils in animal models of autoimmune disease," Seminars in Immunology, Apr. 2016, vol. 28, No. 2, pp. 174-186.

Nunez-Cruz et al., "Genetic and Pharmacologic Inhibition of Complement Impairs Endothelial Cell Function and Ablates Ovarian Cancer Neovascularization," Neoplasia, Nov. 2012, vol. 14, No. 11, pp. 994-1004.

Okroj et al., "Functional Analyses of Complement Convertases Using C3 and CS-Depleted Sera," PLoS One, Oct. 2012, vol. 7, No. 10, e47245, pp. 1-13.

Allegretti et al., "Targeting C5a: Recent Advances in Drug Discovery," Current Medicinal Chemistry, 2005, vol. 12, No. 2, pp. 217-236.

Anonymous, "Emergency Use Authorization (EUA) for Vilobeli mab (IFX-1) Center for Drug Evaluation and Research (CDER) Review," Feb. 1, 2023, 105 pages, Retrieved from the Internet on Dec. 5, 2023; URL: <https://www.gohibic.com/>.

Anonymous, "No significant treatment effect found for IFX-1 in hidradenitis suppurativa trial," Jun. 7, 2019, retrieved from the Internet on Nov. 12, 2019, <https://www.healio.com/dermatology/skin-care/news/online/{72df4fe7-aec-41b0-be1f-0179ed471924}/no-significant-treatment-effect-found-for-ifx-1-in-hidradenitis-suppurativa-trial> (2 pages).

Argyropoulou et al., "An Open-Label Trial to Assess the Safety of IFX-1 in Patients with Hidradenitis Suppurativa not Eligible for Adalimumab," Aug. 4, 2017, poster (1 page).

Beinrohr et al., "C1, MBL-MASPs and C1-inhibilor: novel approaches for targeting complement-mediated inflammation," Trends in Molecular Medicine, 2008, vol. 14, No. 12, pp. 511-521.

Bekker et al., "Characterization of Pharmacologic and Pharmacokinelic Properties of CCX168, a Potent and Selective Orally Administered Complement 5a Receptor Inhibitor, Based on Preclinical Evaluation and Randomized Phase 1 Clinical Study," PLoS One, Oct. 21, 2016, vol. 11, No. 10, e0164646, pp. 1-19.

Biedermann et al., "Regulation of T cell immunity in atopic dermatitis by microbes: the Yin and Yang of cutaneous inflammalion," Frontiers in Immunology, Jul. 13, 2015, vol. 6, Article 353, pp. 1-9.

Binz et al., "Engineering novel binding proteins from nonimmunoglobulin domains," Nature Biotechnology, Oct. 2005, vol. 23, No. 10, pp. 1257-1268.

Blok et al., "Gene expression profiling of skin and blood in hidradenitis suppurativa," British Journal of Dermatology, 2016, vol. 174, pp. 1392-1394.

Braun-Falco et al., "Pyoderma gangrenosum, acne, and suppuralive hidradenitis (PASH)—a new autoinflammatory syndrome distinct from PAPA syndrome," Journal of the American Academy of Dermatology, Mar. 2012, vol. 66, No. 3, pp. 409-415.

Brody et al., "Aptamers as therapeutic and diagnostic agents," Reviews in Molecular Biotechnology, 2000, vol. 74, pp. 5-13.

Buchwald et al., "Long-term, continuous intravenous heparin administration by an implantable infusion pump in ambulatory patients with recurrent venous thrombosis," Surgery, Oct. 1980, vol. 88, No. 4, pp. 507-516.

Cannon, Joseph G., "Analog Design," Chapter 19 in Burger's Medicinal Chemistry and Drug Discovery, 5th Edition, vol. I: Principles and Practice, 1995, pp. 783-802.

Carvelli et al., "Association of COVID-19 inflammation with activation of the C5a-C5aR1 axis," Nature, Dec. 2020, vol. 588, pp. 146-150.

Carvelli et al., "Identification of immune checkpoints in COVID-19," Research Square, 2020, pp. 1-30.

Chen et al., "Enhancement and destruction of antibody function by somatic mutation: unequal occurrence is controllec by V gene combinatorial associations," The EMBO Journal, 1995, vol. 14, No. 12, pp. 2784-2794.

Chen et al., "Plasma proteome of severe acute respiratory syndrome analyzed by two-dimensional gel electrophoresis and mass spectrometry," Proceedings of the National Academy of Sciences of the United States of America, Dec. 7, 2004, vol. 101, No. 49, pp. 17039-17044.

ClinicalTrials.gov archive, "History of Changes for Study: NCT03001622, Studying Complement Inhibition in Patients With Moderate to Severe Hidradenitis Suppurativa," Study NCT03001622, Submitted Dale: Dec. 20, 2016 (v1), pp. 1-5.

ClinicalTrials.gov archive, "History of Changes for Study: NCT03001622, Studying Complement Inhibition in Patients With Moderate to Severe Hidradenitis Suppurativa," Study NCT03001622, Submitted Dale: Mar. 20, 2017 (v3), pp. 1-6.

Cole et al., "Beyond lysis: how complement influences cell fate," Clinical Science, 2003, vol. 104, pp. 455-466.

Colman, P. M., "Effects of amino acid sequence changes on antibody-antigen interactions," Research in Immunology, Jan. 1994, vol. 145, No. 1, pp. 33-36.

Cugno et al., "PAPA, PASH and PAPASH Syndromes: Palhophysiology, Presentation and Treatment," American Journal of Clinical Dermatology, Feb. 2017, vol. 18, pp. 555-562.

Cumpelik et al., "Neutrophil microvesicles resolve gout by inhibiting C5a-medialed priming of the inflammasome," Annals of the Rheumatic Diseases, 2016, vol. 75, No. 6, pp. 1236-1245.

Czermak et al., "Protective effects of C5a blockade in sepsis," Nature Medicine, Jul. 1999, vol. 5, No. 7, pp. 788-792.

Dang et al., "Role of the complement anaphylaloxin C5a-receptor pathway in atopic dermatitis in mice," Molecular Medicine Reports, 2015, vol. 11, pp. 4183-4189.

D'Angelo et al., "Many Routes to an Antibody Heavy-Chain CDR3: Necessary, yet Insufficient, for Specific Binding," Frontiers in Immunology, Mar. 2018, vol. 9, Article 395, pp. 1-13.

Dhingra et al., "Attenuated neutrophil axis in atopic dermatitis compared to psoriasis reflects TH17 pathway differences between these diseases," Journal of Allergy and Clinical Immunology, Aug. 2013, vol. 132, No. 2, pp. 1-7.

Drosten et al., "Identification of a Novel Coronavirus in Patients with Severe Acute Respiratory Syndrome," The New England Journal of Medicine, May 15, 2003, vol. 348, No. 20, pp. 1967-1976.

(56) References Cited

OTHER PUBLICATIONS

Dunkelberger et al., "Complement and its role in innate and adaptive immune responses," Cell Research, 2010, vol. 20, pp. 34-50.

During et al., "Controlled Release of Dopamine from a Polymeric Brain Implant: In Vivo Characterization," Annals of Neurology, Apr. 1989, vol. 25, No. 4, pp. 351-356.

Finch et al., "Low-Molecular-Weight Peptidic and Cyclic Antagonists of the Receptor for the Complement Factor C5a," Journal of Medicinal Chemistry, 1999, vol. 42, No. 11, pp. 1965-1974.

Gál et al., "A True Autoactivating Enzyme: Structural Insight into Mannose-Binding Lectin-Associated Serine Protease-2 Activations," The Journal of Biological Chemistry, Sep. 30, 2005, vol. 280, No. 39, pp. 33435-33444.

Gao et al., "Expression in *Escherichia coli* and Purification of Full Length Recombinant Human MASP2," Letters in Biotechnology, Nov. 2011, vol. 22, No. 6, pp. 806-808 and 891. [English Abstract].

Garcia et al., "Complement C5 Activation during Influenza A Infection in Mice Contributes to Neutrophil Recruitment and Lung Injury," PLoS One, May 2013, vol. 8, No. 5, e64443, pp. 1-11.

Giamarellos-Bourboulis et al., "Abstract: 003-2 I Complement activation in hidradenitis suppurativa," Experimental Dermatology, 2017, vol. 26, Suppl. 1, pp. 3-38.

Goodson, J. Max, "Dental Applications," Medical Applications of Controlled Release, 1984, vol. II, Chapter 6, pp. 115-138.

Graille et al., "CA206: PAPA, PASH, PAPASH, PsAPASH, PASS . . . des syndromes auto-inflammatoires PAS si simples," La Revue de Medecine Interne, 2015, vol. 36, pp. A205-A206.

Gralinski et al., "Complement Activation Contributes to Severe Acute Respiratory Syndrome Coronavirus Pathogenesis," mBio, Sep./Oct. 2018, vol. 9, No. 5, e01753-18, pp. 1-15.

Almagro et al., "Humanization of antibodies," Frontiers in Bioscience, Jan. 1, 2008, vol. 13, pp. 1619-1633.

Altschul et al., "Basic Local Alignment Search Tool," Journal of Molecular Biology, 1990, vol. 215, pp. 403-410.

Altschul et al., "Gapped BLAST and PSI-BLAST: a new generation of protein database search programs," Nucleic Acids Research, 1997, vol. 25, No. 17, pp. 3389-3402.

Bird et al., "Single-Chain Antigen-Binding Proteins," Science, Oct. 21, 1988, vol. 242, pp. 423-426.

Brudno et al., "Glocal alignment: finding rearrangements during alignment," Bioinformatics, 2003, vol. 19, Suppl. 1, pp. i54-i62.

Bryson et al., "Prediction of Immunogenicity of Therapeutic Proteins: Validity of Computational Tools," Biodrugs, 2010, vol. 24, Article No. 1, pp. 1-8.

Czermak et al., "In Vitro and In Vivo Dependency of Chemokine Generation on C5a and TNF-α," The Journal of Immunology, 1999, vol. 162, No. 4, pp. 2321-2325.

Guo et al., "Role of C5a in Inflammatory Responses," Annual Review of Immunology, 2005, vol. 23, pp. 821-852.

Guo et al., "C5a, a Therapeutic Target in Sepsis," Recent Patents on Anti-Infective Drug Discovery, 2006, vol. 1, No. 1, pp. 57-65.

Heap et al., "Analysis of a 17-amino acid residue, virus-neutralizing microantibody," Journal of General Virology, 2005, vol. 86, pp. 1791-1800.

Holliger et al., ""Diabodies": Small bivalent and bispecific antibody fragments," Proceedings of the National Academy of Sciences of the United States of America, Jul. 1993, vol. 90, pp. 6444-6448.

Hu et al., "Large-scale mammalian cell culture," Current Opinion in Biotechnology, 1997, vol. 8, pp. 148-153.

Huber-Lang et al., "Complement-Induced Impairment of Innate Immunity During Sepsis," The Journal of Immunology, 2002, vol. 169, No. 6, pp. 3223-3231.

Huber-Lang et al., "Role of C5a in Multiorgan Failure During Sepsis," The Journal of Immunology, 2001, vol. 166, No. 2, pp. 1193-1199.

Huston et al., "Protein engineering of antibody binding sites: Recovery of specific activity in an anti-digoxin single-chain Fv analogue produced in *Escherichia coli*," Proceedings of the National Academy of Sciences of the United States of America, Aug. 1988, vol. 85, pp. 5879-5883.

Karlin et al., "Applications and statistics for multiple high-scoring segments in molecular sequences," Proceedings of the National Academy of Sciences of the United States of America, Jun. 1993, vol. 90, pp. 5873-5877.

Klos et al., "Detection of native human complement components C3 and C5 and their primary activation peptides C3a and C5a (anaphylatoxic peptides) by ELISAs with monoclonal antibodies," Journal of Immunological Methods, 1988, vol. 111, pp. 241-252.

Larkin et al., "Clustal W and Clustal X version 2.0," Bioinformatics, 2007, vol. 23, No. 21, pp. 2947-2948.

Pawaria et al., "Complement Component C5a Permits the Coexistence of Pathogenic Th17 Cells and Type I IFN in Lupus," The Journal of Immunology, 2014, vol. 193, No. 7, pp. 3288-3295.

Perry et al., "New Approaches to Prediction of Immune Responses to Therapeutic Proteins during Preclinical Development," Drugs in R & D, 2008, vol. 9, No. 6, pp. 385-396.

Qiu et al., "Small antibody mimetics comprising two complementarity-determining regions and a framework region for tumor targeting," Nature Biotechnology, 2007, vol. 25, No. 8, pp. 921-929.

Riedemann et al., "Increased C5a receptor expression in sepsis," The Journal of Clinical Investigation, Jul. 2002, vol. 110, No. 1, pp. 101-108.

Rittirsch et al., "Functional roles for C5a receptors in sepsis," Nature Medicine, May 2008, vol. 14, No. 5, pp. 551-557.

Strainic et al., "Absent C3a and C5a receptor signaling into CD4+ T cells enables auto-inductive TGF-β1 signaling and induction of Foxp3+ T regulatory cells," Nature Immunology, Feb. 2013, vol. 14, No. 2, pp. 162-171.

Thompson et al., "Clustal W: improving the sensitivity of progressive multiple sequence alignment through sequence weighting, position-specific gap penalties and weight matrix choice," Nucleic Acids Research, 1994, vol. 22, No. 22, pp. 4673-4680.

Ward et al., "Binding activities of a repertoire of single immunoglobulin variable domains secreted from *Escherichia coli*," Nature, Oct. 12, 1989, vol. 341, pp. 544-546.

Ward, Peter A., "Functions of C5a receptors," Journal of Molecular Medicine, Apr. 2009, vol. 87, No. 4, pp. 375-378.

Xu et al., "Interleukin-17 and its expanding biological functions," Cellular & Molecular Immunology, 2010, vol. 7, pp. 164-174.

Holgate et al., "Circumventing immunogenicity in the development of therapeutic antibodies," IDrugs, 2009, vol. 12, No. 4, pp. 233-237.

International Search Report and Written Opinion mailed Jul. 28, 2021 in corresponding International PCT Patent Application No. PCT/EP2021/061940 (10 pages).

Oppermann et al., "Probing the Human Receptor for C5a Anaphylatoxin with Site-Directed Antibodies: Identification of a Potential Ligand Binding Site on the NH2-Terminal Domain," The Journal of Immunology, Oct. 1993, vol. 151, No. 7, pp. 3785-3794.

Pang et al., "Serum Proteomic Fingerprints of Adult Patients with Severe Acute Respiratory Syndrome," Clinical Chemistry, 2006, vol. 52, No. 3, pp. 421-429.

Petersen et al., "An assay for the mannan-binding lectin pathway of complement activation," Journal of Immunological Methods, 2001, vol. 257, pp. 107-116.

Petitclerc et al., "Pathologic Leukocyte Infiltration of the Rabbit Aorta Confers a Vasomotor Effect to Chemotactic Peptides Through Cyclooxygenase-Derived Metabolites," The Journal of Immunology, May 1996, vol. 156, No. 9, pp. 3426-3434.

Piche-Nicholas et al., "Changes in complementarity-determining regions significantly alter IgG binding to the neonatal Fe receptor (FcRn) and pharmacokinetics," MABS, 2018, vol. 10, No. 1, pp. 81-94.

Prat et al., "Neutrophilic dermatoses as systemic diseases," Clinics in Dermatology, 2014, vol. 32, No. 3, pp. 376-388.

Proctor et al., "Transdermal Pharmacology of Small Molecule Cyclic C5a Antagonists," Advances in Experimental Medicine and Biology, 2006, vol. 586, pp. 329-345.

Rawal et al., "Activation of Complement Component C5: Comparison of C5 Convertases of the Lectin Pathway and the Classical

(56) References Cited

OTHER PUBLICATIONS

Pathway of Complement," The Journal of Biological Chemistry, Mar. 21, 2008, vol. 283, No. 12, pp. 7853-7863.

RCSB Protein 4UU9: Crystal structure of the human c5a in complex with MEDI7814 a neutralising antibody; retrieved from the Internet on May 26, 2023, pp. 1-5.

Ren et al., "The use of proteomics in the discovery of serum biomarkers from patients with severe acute respiratory syndrome," Proteomics, 2004, vol. 4, No. 11, pp. 3477-3484.

Revuz, J., "Hidradenitis suppurativa," Journal of the European Academy of Dermatology and Venereology, 2009, vol. 23, No. 9, pp. 985-998.

Ricardo et al., "Preclinical Evaluation of RA 101495, a Potent Cyclic Peptide Inhibitor of C5 for the Treatment of Paroxysmal Nocturnal Hemoglobinuria," Blood, 2015, vol. 126, No. 23, p. 939.

Ricklin et al., "The renaissance of complement therapeutics," Nature Reviews: Nephrology, Jan. 2018, vol. 14, pp. 26-47.

Riedemann et al., "Controlling the anaphylatoxin C5a in diseases requires a specifically targeted inhibition," Clinical Immunology, 2017, vol. 180, pp. 25-32.

Riedemann et al., "Expression and Function of the C5a Receptor in Rat Alveolar Epithelial Cells," The Journal of Immunology, 2002, vol. 168, pp. 1919-1925.

Riedemann et al., "Regulatory Role of C5a on Macrophage Migration Inhibitory Factor Release from Neutrophils," The Journal of Immunology, 2004, vol. 173, pp. 1355-1359.

Rittirsch et al., "Harmful molecular mechanisms in sepsis," Nature Reviews Immunology, Oct. 2008, vol. 8, pp. 776-787.

Rudikoff et al., "Single amino acid substitution altering antigen-binding specificity," Proceedings of the National Academy of Sciences of the United States of America, Mar. 1982, vol. 79, pp. 1979-1983.

Samaee et al., "Tocilizumab for treatment patients with COVID-19: Recommended medication for novel disease," International Immunopharmacology, 2020, vol. 89, Article No. 107018, pp. 1-7.

Sánchez-Galán et al., "Leukotriene B4 enhances the activity of nuclear factor-kB pathway through BLT1 and BLT2 receptors in atherosclerosis," Cardiovascular Research, 2009, vol. 81, pp. 216-225.

Sarma et al., "Complement in lung disease," Autoimmunity, Aug. 2006, vol. 39, No. 5, pp. 387-394.

Saudek et al., "A Preliminary Trial of the Programmable Implantable Medication System for Insulin Delivery," The New England Journal of Medicine, Aug. 31, 1989, vol. 321, No. 9, pp. 574-579.

Schatz-Jakobsen et al., "Structural and functional characterization of human and murine C5a anaphylatoxins," Acta Crystallographica Section D Biological Crystallography, Jun. 2014, vol. 70, Pl. 6, pp. 1704-1717.

Schwaeble et al., "Targeting of mannan-binding lectin-associated serine protease-2 confers protection from myocardial and gastrointestinal ischemia/reperfusion injury," Proceedings of the National Academy of Sciences of the United States of America, May 3, 2011, vol. 108, No. 18, pp. 7523-7528.

Sefton, Michael V., "Implantable Pumps," CRC Critical Reviews in Biomedical Engineering, 1987, vol. 14, No. 3, pp. 201-240.

Slade et al., "Hidradenitis suppurativa: pathogenesis and management," British Journal of Plastic Surgery, 2003, vol. 56, No. 5, pp. 451-461.

Smith, Kristen, "If at first you don't succeed . . . ," Jul. 2019; retrieved from the Internet on Nov. 12, 2019 <https://www.ddn-news.com/index.php?newsarticle=13478> (2 pages).

Song et al., "C5a receptor1 inhibition alleviates influenza virus-induced acute lung injury," International Immunopharmacology, 2018, vol. 59, pp. 12-20.

Souza et al., "APT070 (Mirococept), a membrane-localised complement inhibitor, inhibits inflammatory responses that follow intesti-nal ischaemia and reperfusion injury," British Journal of Pharmacology, 2005, vol. 145, No. 8, pp. 1027-1034.

Strainic et al., "Absent C3a and C5a receptor signaling into CD4+ T cells enables auto-inductive TGF-B1 signaling and induction of Foxp3+ T regulatory cells," Nature Immunology, Feb. 2013, vol. 14, No. 2, pp. 162-171.

Strieter et al., "Cytokine-induced Neutrophil-derived Interleukin-8," American Journal of Pathology, Aug. 1992, vol. 141, No. 2, pp. 397-407.

Sun et al., "Inhibition of Complement Activation Alleviates Acute Lung Injury Induced by Highly Pathogenic Avian Influenza H5N1 Virus Infection," American Journal of Respiratory Cell and Molecular Biology, Aug. 2013, vol. 49, No. 2, pp. 221-230.

Sun et al., "Treatment With Anti-C5a Antibody Improves the Outcome of H7N9 Virus Infection in African Green Monkeys," Clinical Infectious Diseases, 2015, vol. 60, No. 4, pp. 586-595.

Tagami, "Recent topics in sterile pustular dermatoses," Japanese Journal of Inflammation, 1986, vol. 6, No. 1, pp. 5-14. [English Abstract].

Takahashi et al., "The mannose-binding lectin: a prototypic pattern recognition molecule," Current Opinion in Immunology, 2006, vol. 18, pp. 16-23.

Tang et al., "Abnormal coagulation parameters are associated with poor prognosis in patients with novel coronavirus pneumonia," Journal of Thrombosis and Haemostasis, 2020, vol. 18, pp. 844-847.

Tang et al., "Anticoagulant treatment is associated with decreased mortality in severe coronavirus disease 2019 patients with coagulopathy," Journal of Thrombosis and Haemostasis, 2020, vol. 18, pp. 1094-1099.

Taylor, Phil, "InflaRx flatlines after skin disease drug flops in midstage trial," pharmaphorum, Jun. 6, 2019; retrieved from the Internet on Nov. 12, 2019 <hllps://pharmaphorum.com/news/inflarx-flatlines-skin-disease-drugmidstage-trial/> (2 pages).

Ternowitz et al., "Methotrexate Inhibits the Human C5a-Induced Skin Response in Patients with Psoriasis," The Journal of Investigative Dermatology, Aug. 1987, vol. 89, No. 2, pp. 192-196.

Tesar et al., "Avacopan in the treatment of ANCA-associated vasculitis," Expert Opinion on Investigational Drugs, 2018, vol. 27, No. 5, pp. 491-496.

Treat et al., "Liposome Encapsulated Doxorubicin Preliminary Results of Phase I and Phase II Trials," Liposomes in the Therapy of Infectious Diseases and Cancer, Lopez-Berestein and Fidler (eds.), 1989, pp. 353-365.

Tzanetakou et al., "Safety and Efficacy of Anakinra in Severe Hidradenitis Suppurativa: A Randomized Clinical Trial," JAMA Dermatology, 2016, vol. 152, No. 1, pp. 52-59.

UniProtKB P01031: C05_Human; retrieved from the Internet on May 26, 2023 (13 pages).

UniProtKB P05231: IL6_Human; retrieved from the Internet on May 26, 2023 (12 pages).

USBiological Life Sciences Certificate of Analysis for Antibody Clone No. 7H110 (Mouse Anti-Human COBB Antibody), Date of Manufacture: May 17, 2017 (1 page).

Verdolini et al., "Metformin for the treatment of hidradenitis suppurativa: a little help along the way," Journal of the European Academy of Dermatology and Venereology, 2013, vol. 27, No. 9, pp. 1101-1108.

Vlaar et al., "Anti-C5a antibody IFX-1 (vilobelimab) treatment versus best supportive care for patients with severe COVID-19 (PANAMO): an exploratory, open-label, phase 2 randomised controlled trial," The Lancet Rheumatology, Dec. 2020, vol. 2, pp. e764-e773.

Wallis, Russell, "Interactions between mannose-binding lectin and MASPs during complement activation by the lectin pathway," Immunobiology, 2007, vol. 212, pp. 289-299.

* cited by examiner

IFX concentration (ng/mL)

SEQUENCE LISTING

<160> NUMBER OF SEQ ID NOS: 25

<210> SEQ ID NO 1
<211> LENGTH: 74
<212> TYPE: PRT
<213> ORGANISM: Homo sapiens

<400> SEQUENCE: 1

Thr Leu Gln Lys Lys Ile Glu Glu Ile Ala Ala Lys Tyr Lys His Ser
1               5                   10                  15

-continued

```
Val Val Lys Lys Cys Cys Tyr Asp Gly Ala Cys Val Asn Asn Asp Glu
          20                  25                  30

Thr Cys Glu Gln Arg Ala Ala Arg Ile Ser Leu Gly Pro Arg Cys Ile
          35                  40                  45

Lys Ala Phe Thr Glu Cys Cys Val Val Ala Ser Gln Leu Arg Ala Asn
          50                  55                  60

Ile Ser His Lys Asp Met Gln Leu Gly Arg
65                  70
```

```
<210> SEQ ID NO 2
<211> LENGTH: 9
<212> TYPE: PRT
<213> ORGANISM: Homo sapiens

<400> SEQUENCE: 2

Asn Asp Glu Thr Cys Glu Gln Arg Ala
1                   5
```

```
<210> SEQ ID NO 3
<211> LENGTH: 7
<212> TYPE: PRT
<213> ORGANISM: Homo sapiens

<400> SEQUENCE: 3

Ser His Lys Asp Met Gln Leu
1                   5
```

```
<210> SEQ ID NO 4
<211> LENGTH: 7
<212> TYPE: PRT
<213> ORGANISM: Homo sapiens

<400> SEQUENCE: 4

Asp Glu Thr Cys Glu Gln Arg
1                   5
```

```
<210> SEQ ID NO 5
<211> LENGTH: 5
<212> TYPE: PRT
<213> ORGANISM: Homo sapiens

<400> SEQUENCE: 5

His Lys Asp Met Gln
1                   5
```

```
<210> SEQ ID NO 6
<211> LENGTH: 119
<212> TYPE: PRT
<213> ORGANISM: Artificial Sequence
<220> FEATURE:
<223> OTHER INFORMATION: VH0

<400> SEQUENCE: 6

Gln Val Gln Leu Gln Gln Ser Gly Pro Gln Leu Val Arg Pro Gly Thr
1                   5                  10                  15

Ser Val Lys Ile Ser Cys Lys Ala Ser Gly Tyr Ser Phe Thr Thr Phe
          20                  25                  30

Trp Met Asp Trp Val Lys Gln Arg Pro Gly Gln Gly Leu Glu Trp Ile
          35                  40                  45

Gly Arg Ile Asp Pro Ser Asp Ser Glu Ser Arg Leu Asp Gln Arg Phe
          50                  55                  60

Lys Asp Arg Ala Thr Leu Thr Val Asp Lys Ser Ser Ser Thr Val Tyr
```

-continued

```
65                      70                      75                      80

Met Gln Leu Ser Ser Pro Thr Ser Glu Asp Ser Ala Val Tyr Tyr Cys
                85                      90                      95

Ala Arg Gly Asn Asp Gly Tyr Tyr Gly Phe Ala Tyr Trp Gly Gln Gly
            100                     105                     110

Thr Leu Val Thr Val Ser Ser
            115

<210> SEQ ID NO 7
<211> LENGTH: 119
<212> TYPE: PRT
<213> ORGANISM: Artificial Sequence
<220> FEATURE:
<223> OTHER INFORMATION: VH1

<400> SEQUENCE: 7

Gln Val Gln Leu Val Gln Ser Gly Pro Glu Leu Lys Lys Pro Gly Ala
1               5                       10                      15

Ser Val Lys Ile Ser Cys Lys Ala Ser Gly Tyr Ser Phe Thr Thr Phe
                20                      25                      30

Trp Met Asp Trp Val Lys Gln Ala Pro Gly Gln Gly Leu Glu Trp Ile
            35                      40                      45

Gly Arg Ile Asp Pro Ser Asp Ser Glu Ser Arg Leu Asp Gln Arg Phe
        50                      55                      60

Lys Asp Arg Ala Thr Leu Thr Val Asp Lys Ser Thr Ser Thr Val Tyr
65                      70                      75                      80

Met Gln Leu Ser Ser Pro Thr Ser Glu Asp Ser Ala Val Tyr Tyr Cys
                85                      90                      95

Ala Arg Gly Asn Asp Gly Tyr Tyr Gly Phe Ala Tyr Trp Gly Gln Gly
            100                     105                     110

Thr Leu Val Thr Val Ser Ser
            115

<210> SEQ ID NO 8
<211> LENGTH: 119
<212> TYPE: PRT
<213> ORGANISM: Artificial Sequence
<220> FEATURE:
<223> OTHER INFORMATION: VH2

<400> SEQUENCE: 8

Gln Val Gln Leu Val Gln Ser Gly Ala Glu Val Lys Lys Pro Gly Ala
1               5                       10                      15

Ser Val Lys Ile Ser Cys Lys Ala Ser Gly Tyr Ser Phe Thr Thr Phe
                20                      25                      30

Trp Met Asp Trp Val Lys Gln Ala Pro Gly Gln Gly Leu Glu Trp Ile
            35                      40                      45

Gly Arg Ile Asp Pro Ser Asp Ser Glu Ser Arg Leu Asp Gln Arg Phe
        50                      55                      60

Lys Asp Arg Ala Thr Leu Thr Val Asp Lys Ser Thr Ser Thr Val Tyr
65                      70                      75                      80

Met Glu Leu Ser Ser Leu Arg Ser Glu Asp Thr Ala Val Tyr Tyr Cys
                85                      90                      95

Ala Arg Gly Asn Asp Gly Tyr Tyr Gly Phe Ala Tyr Trp Gly Gln Gly
            100                     105                     110

Thr Leu Val Thr Val Ser Ser
            115
```

<210> SEQ ID NO 9
<211> LENGTH: 119
<212> TYPE: PRT
<213> ORGANISM: Artificial Sequence
<220> FEATURE:
<223> OTHER INFORMATION: VH3

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Thr Phe
            20                  25                  30

Trp Met Asp Trp Val Arg Gln Ala Pro Gly Gln Gly Leu Glu Trp Ile
        35                  40                  45

Gly Arg Ile Asp Pro Ser Asp Ser Glu Ser Arg Leu Asp Gln Arg Phe
    50                  55                  60

Lys Asp Arg Ala Thr Leu Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asn Asp Gly Tyr Tyr Gly Phe Ala Tyr Trp Gly Gln Gly
            100                 105                 110

Thr Leu Val Thr Val Ser Ser
        115

<210> SEQ ID NO 10
<211> LENGTH: 119
<212> TYPE: PRT
<213> ORGANISM: Artificial Sequence
<220> FEATURE:
<223> OTHER INFORMATION: VH4

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Thr Phe
            20                  25                  30

Trp Met Asp Trp Val Arg Gln Ala Pro Gly Gln Gly Leu Glu Trp Ile
        35                  40                  45

Gly Arg Ile Asp Pro Ser Asp Ser Glu Ser Arg Leu Asp Gln Arg Phe
    50                  55                  60

Lys Asp Arg Val Thr Met Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asn Asp Gly Tyr Tyr Gly Phe Ala Tyr Trp Gly Gln Gly
            100                 105                 110

Thr Leu Val Thr Val Ser Ser
        115

<210> SEQ ID NO 11
<211> LENGTH: 119
<212> TYPE: PRT
<213> ORGANISM: Artificial Sequence
<220> FEATURE:
<223> OTHER INFORMATION: VH5

<400> SEQUENCE: 11

Gln Val Gln Leu Val Gln Ser Gly Ala Glu Val Lys Lys Pro Gly Ala

```
1                  5                  10                 15

Ser Val Lys Val Ser Cys Lys Ala Ser Gly Tyr Ser Phe Thr Thr Phe
         20                 25                 30

Trp Met Asp Trp Val Arg Gln Ala Pro Gly Gln Gly Leu Glu Trp Met
         35                 40                 45

Gly Arg Ile Asp Pro Ser Asp Ser Glu Ser Arg Leu Asp Gln Lys Phe
    50                 55                 60

Lys Asp Arg Val Thr Met Thr Val Asp Lys Ser Thr Ser Thr Val Tyr
65                 70                 75                 80

Met Glu Leu Ser Ser Leu Arg Ser Glu Asp Thr Ala Val Tyr Tyr Cys
                   85                 90                 95

Ala Arg Gly Asn Asp Gly Tyr Tyr Gly Phe Ala Tyr Trp Gly Gln Gly
             100                105                110

Thr Leu Val Thr Val Ser Ser
         115
```

<210> SEQ ID NO 12
<211> LENGTH: 111
<212> TYPE: PRT
<213> ORGANISM: Artificial Sequence
<220> FEATURE:
<223> OTHER INFORMATION: V_kappa_0

<400> SEQUENCE: 12

```
Asp Ile Val Leu Thr Gln Ser Pro Ala Ser Leu Ala Val Ser Leu Gly
1                  5                  10                 15

Gln Arg Ala Thr Ile Ser Cys Lys Ala Ser Gln Ser Val Asp Tyr Asp
         20                 25                 30

Gly Asp Ser Tyr Met Lys Trp Tyr Gln Gln Lys Pro Gly Gln Pro Pro
         35                 40                 45

Lys Leu Leu Ile Tyr Ala Ala Ser Asn Leu Gln Ser Gly Ile Pro Ala
    50                 55                 60

Arg Phe Ser Gly Ser Gly Ser Gly Thr Asp Phe Thr Leu Asn Ile His
65                 70                 75                 80

Pro Val Glu Glu Glu Asp Ala Ala Thr Tyr Tyr Cys Gln Gln Ser Asn
                   85                 90                 95

Glu Asp Pro Tyr Thr Phe Gly Gly Gly Thr Lys Leu Glu Ile Lys
             100                105                110
```

<210> SEQ ID NO 13
<211> LENGTH: 111
<212> TYPE: PRT
<213> ORGANISM: Artificial Sequence
<220> FEATURE:
<223> OTHER INFORMATION: V_kappa_1

<400> SEQUENCE: 13

```
Asp Ile Val Leu Thr Gln Ser Pro Ala Ser Leu Ala Ala Ser Val Gly
1                  5                  10                 15

Asp Arg Val Thr Ile Thr Cys Lys Ala Ser Gln Ser Val Asp Tyr Asp
         20                 25                 30

Gly Asp Ser Tyr Met Lys Trp Tyr Gln Gln Lys Pro Gly Lys Ala Pro
         35                 40                 45

Lys Leu Leu Ile Tyr Ala Ala Ser Asn Leu Gln Ser Gly Ile Pro Ser
    50                 55                 60

Arg Phe Ser Gly Ser Gly Ser Gly Thr Asp Phe Thr Leu Thr Ile Ser
65                 70                 75                 80
```

```
Ser Leu Gln Glu Glu Asp Phe Ala Thr Tyr Tyr Cys Gln Gln Ser Asn
                85                  90                  95

Glu Asp Pro Tyr Thr Phe Gly Gln Gly Thr Lys Leu Glu Ile Lys
            100                 105                 110

<210> SEQ ID NO 14
<211> LENGTH: 111
<212> TYPE: PRT
<213> ORGANISM: Artificial Sequence
<220> FEATURE:
<223> OTHER INFORMATION: V_kappa_2

<400> SEQUENCE: 14

Asp Ile Val Leu Thr Gln Ser Pro Ala Ser Leu Ser Ala Ser Val Gly
1               5                   10                  15

Asp Arg Val Thr Ile Thr Cys Lys Ala Ser Gln Ser Val Asp Tyr Asp
                20                  25                  30

Gly Asp Ser Tyr Met Lys Trp Tyr Gln Gln Lys Pro Gly Lys Ala Pro
            35                  40                  45

Lys Leu Leu Ile Tyr Ala Ala Ser Asn Leu Gln Ser Gly Ile Pro Ser
        50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Tyr Thr Phe Gly Gln Gly Thr Lys Leu Glu Ile Lys
            100                 105                 110

<210> SEQ ID NO 15
<211> LENGTH: 111
<212> TYPE: PRT
<213> ORGANISM: Artificial Sequence
<220> FEATURE:
<223> OTHER INFORMATION: V_kappa_3

<400> SEQUENCE: 15

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
                20                  25                  30

Gly Asp Ser Tyr Met Lys Trp Tyr Gln Gln Lys Pro Gly Lys Ala Pro
            35                  40                  45

Lys Leu Leu Ile Tyr Ala Ala Ser Asn Leu Gln Ser Gly Ile Pro Ser
        50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Tyr Thr Phe Gly Gln Gly Thr Lys Leu Glu Ile Lys
            100                 105                 110

<210> SEQ ID NO 16
<211> LENGTH: 111
<212> TYPE: PRT
<213> ORGANISM: Artificial Sequence
<220> FEATURE:
<223> OTHER INFORMATION: V_kappa_4

<400> SEQUENCE: 16

Asp Ile Gln Met Thr Gln Ser Pro Ser Ser Leu Ser Ala Ser Val Gly
```

-continued

```
1               5               10              15

Asp Arg Val Thr Ile Thr Cys Lys Ala Ser Gln Ser Val Asp Tyr Asp
            20              25              30

Gly Asp Ser Tyr Met Lys Trp Tyr Gln Gln Lys Pro Gly Lys Ala Pro
            35              40              45

Lys Leu Leu Ile Tyr Ala Ala Ser Asn Leu Gln Ser Gly Val Pro Ser
    50              55              60

Arg Phe Ser Gly Ser Gly Ser Gly Thr Asp Phe Thr Leu Thr Ile Ser
65              70              75              80

Ser Leu Gln Pro Glu Asp Phe Ala Thr Tyr Tyr Cys Gln Gln Ser Asn
                85              90              95

Glu Asp Pro Tyr Thr Phe Gly Gln Gly Thr Lys Leu Glu Ile Lys
                100             105             110
```

```
<210> SEQ ID NO 17
<211> LENGTH: 119
<212> TYPE: PRT
<213> ORGANISM: Artificial Sequence
<220> FEATURE:
<223> OTHER INFORMATION: Consensus sequence formed from the combination
      of VH1 to VH5
<220> FEATURE:
<221> NAME/KEY: MISC_FEATURE
<222> LOCATION: (9)..(9)
<223> OTHER INFORMATION: Xaa9 is A or P
<220> FEATURE:
<221> NAME/KEY: MISC_FEATURE
<222> LOCATION: (11)..(11)
<223> OTHER INFORMATION: Xaa11 is L or P
<220> FEATURE:
<221> NAME/KEY: MISC_FEATURE
<222> LOCATION: (20)..(20)
<223> OTHER INFORMATION: Xaa20 is I or V
<220> FEATURE:
<221> NAME/KEY: MISC_FEATURE
<222> LOCATION: (38)..(38)
<223> OTHER INFORMATION: Xaa38 is K or R
<220> FEATURE:
<221> NAME/KEY: MISC_FEATURE
<222> LOCATION: (48)..(48)
<223> OTHER INFORMATION: Xaa48 is I or M
<220> FEATURE:
<221> NAME/KEY: MISC_FEATURE
<222> LOCATION: (63)..(63)
<223> OTHER INFORMATION: Xaa63 is K or R
<220> FEATURE:
<221> NAME/KEY: MISC_FEATURE
<222> LOCATION: (68)..(68)
<223> OTHER INFORMATION: Xaa68 is A or V
<220> FEATURE:
<221> NAME/KEY: MISC_FEATURE
<222> LOCATION: (70)..(70)
<223> OTHER INFORMATION: Xaa70 is L or M
<220> FEATURE:
<221> NAME/KEY: MISC_FEATURE
<222> LOCATION: (82)..(82)
<223> OTHER INFORMATION: Xaa82 is E or Q
<220> FEATURE:
<221> NAME/KEY: MISC_FEATURE
<222> LOCATION: (86)..(86)
<223> OTHER INFORMATION: Xaa86 is L or P
<220> FEATURE:
<221> NAME/KEY: MISC_FEATURE
<222> LOCATION: (87)..(87)
<223> OTHER INFORMATION: Xaa87 is R or T
<220> FEATURE:
<221> NAME/KEY: MISC_FEATURE
<222> LOCATION: (91)..(91)
<223> OTHER INFORMATION: Xaa91 is S or T

<400> SEQUENCE: 17
```

-continued

```
Gln Val Gln Leu Val Gln Ser Gly Xaa Glu Xaa Lys Lys Pro Gly Ala
1                   5                   10                  15

Ser Val Lys Xaa Ser Cys Lys Ala Ser Gly Tyr Ser Phe Thr Thr Phe
                20                  25                  30

Trp Met Asp Trp Val Xaa Gln Ala Pro Gly Gln Gly Leu Glu Trp Xaa
                35                  40                  45

Gly Arg Ile Asp Pro Ser Asp Ser Glu Ser Arg Leu Asp Gln Xaa Phe
        50                  55                  60

Lys Asp Arg Xaa Thr Xaa Thr Val Asp Lys Ser Thr Ser Thr Val Tyr
65                  70                  75                  80

Met Xaa Leu Ser Ser Xaa Xaa Ser Glu Asp Xaa Ala Val Tyr Tyr Cys
                85                  90                  95

Ala Arg Gly Asn Asp Gly Tyr Tyr Gly Phe Ala Tyr Trp Gly Gln Gly
            100                 105                 110

Thr Leu Val Thr Val Ser Ser
            115
```

<210> SEQ ID NO 18
<211> LENGTH: 111
<212> TYPE: PRT
<213> ORGANISM: Artificial Sequence
<220> FEATURE:
<223> OTHER INFORMATION: Consensus sequence formed from the combination
      of V_kappa_1 to V_kappa_4
<220> FEATURE:
<221> NAME/KEY: MISC_FEATURE
<222> LOCATION: (3)..(3)
<223> OTHER INFORMATION: Xaa3 is V or Q
<220> FEATURE:
<221> NAME/KEY: MISC_FEATURE
<222> LOCATION: (4)..(4)
<223> OTHER INFORMATION: Xaa4 is L or M
<220> FEATURE:
<221> NAME/KEY: MISC_FEATURE
<222> LOCATION: (9)..(9)
<223> OTHER INFORMATION: Xaa9 is A or S
<220> FEATURE:
<221> NAME/KEY: MISC_FEATURE
<222> LOCATION: (12)..(12)
<223> OTHER INFORMATION: Xaa12 is A or S
<220> FEATURE:
<221> NAME/KEY: MISC_FEATURE
<222> LOCATION: (62)..(62)
<223> OTHER INFORMATION: Xaa62 is I or V
<220> FEATURE:
<221> NAME/KEY: MISC_FEATURE
<222> LOCATION: (84)..(84)
<223> OTHER INFORMATION: Xaa84 is E or P

<400> SEQUENCE: 18

```
Asp Ile Xaa Xaa Thr Gln Ser Pro Xaa Ser Leu Xaa Ala Ser Val Gly
1                   5                   10                  15

Asp Arg Val Thr Ile Thr Cys Lys Ala Ser Gln Ser Val Asp Tyr Asp
                20                  25                  30

Gly Asp Ser Tyr Met Lys Trp Tyr Gln Gln Lys Pro Gly Lys Ala Pro
            35                  40                  45

Lys Leu Leu Ile Tyr Ala Ala Ser Asn Leu Gln Ser Gly Xaa Pro Ser
    50                  55                  60

Arg Phe Ser Gly Ser Gly Ser Gly Thr Asp Phe Thr Leu Thr Ile Ser
65                  70                  75                  80

Ser Leu Gln Xaa Glu Asp Phe Ala Thr Tyr Tyr Cys Gln Gln Ser Asn
                85                  90                  95

Glu Asp Pro Tyr Thr Phe Gly Gln Gly Thr Lys Leu Glu Ile Lys
            100                 105                 110
```

-continued

```
<210> SEQ ID NO 19
<211> LENGTH: 327
<212> TYPE: PRT
<213> ORGANISM: Homo sapiens

<400> SEQUENCE: 19

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 20
<211> LENGTH: 14
<212> TYPE: PRT
<213> ORGANISM: Artificial Sequence
<220> FEATURE:
<223> OTHER INFORMATION: IFX-1 CDR1 heavy chain
```

-continued

```
<400> SEQUENCE: 20

Cys Lys Ala Ser Gly Tyr Ser Phe Thr Thr Phe Trp Met Asp
1               5                   10

<210> SEQ ID NO 21
<211> LENGTH: 12
<212> TYPE: PRT
<213> ORGANISM: Artificial Sequence
<220> FEATURE:
<223> OTHER INFORMATION: IFX-1 CDR2 heavy chain

<400> SEQUENCE: 21

Ile Asp Pro Ser Asp Ser Glu Ser Arg Leu Asp Gln
1               5                   10

<210> SEQ ID NO 22
<211> LENGTH: 13
<212> TYPE: PRT
<213> ORGANISM: Artificial Sequence
<220> FEATURE:
<223> OTHER INFORMATION: IFX-1 CDR3 heavy chain

<400> SEQUENCE: 22

Cys Ala Arg Gly Asn Asp Gly Tyr Tyr Gly Phe Ala Tyr
1               5                   10

<210> SEQ ID NO 23
<211> LENGTH: 16
<212> TYPE: PRT
<213> ORGANISM: Artificial Sequence
<220> FEATURE:
<223> OTHER INFORMATION: IFX-1 CDR1 light chain

<400> SEQUENCE: 23

Cys Lys Ala Ser Gln Ser Val Asp Tyr Asp Gly Asp Ser Tyr Met Lys
1               5                   10                  15

<210> SEQ ID NO 24
<211> LENGTH: 7
<212> TYPE: PRT
<213> ORGANISM: Artificial Sequence
<220> FEATURE:
<223> OTHER INFORMATION: IFX-1 CDR2 light chain

<400> SEQUENCE: 24

Ile Tyr Ala Ala Ser Asn Leu
1               5

<210> SEQ ID NO 25
<211> LENGTH: 10
<212> TYPE: PRT
<213> ORGANISM: Artificial Sequence
<220> FEATURE:
<223> OTHER INFORMATION: IFX-1 CDR3 light chain

<400> SEQUENCE: 25

Cys Gln Gln Ser Asn Glu Asp Pro Tyr Thr
1               5                   10
```

HUMANIZED ANTI-C5a ANTIBODIES

CROSS-REFERENCE TO RELATED APPLICATIONS

This application is the U.S. National Stage Application, pursuant to 35 U.S.C. § 371 of PCT International Application No. PCT/EP2021/061940, filed May 6, 2021, designating the United States and published in English, which claims the benefit of and priority to European Patent Application No. 20173255.9, filed May 6, 2020, the entire contents of each of which are incorporated herein by reference in their entirety.

FIELD OF THE INVENTION

The present invention relates to antibodies that specifically bind to a conformational epitope of human C5a. The invention particularly relates to humanized anti-C5a antibodies. The antibodies described herein are useful as active agents in pharmaceutical compositions. The antibodies and pharmaceutical compositions are especially useful for the treatment and prevention of diseases or disorders involving pathological C5a activity.

BACKGROUND OF THE INVENTION

C5a

C5a is a 74 amino acid spanning split product of its "mother molecule" C5 and represents one endpoint of the complement activation cascade. It can be generated through activation of at least three well-described pathways (the alternative, the classical and the MBL pathway). All pathways merge at the level of C3, forming the C5- or alternative C5 convertase leading to cleavage of C5 into C5a and C5b. The latter binds with C6, C7, C8 and multiple C9 molecules ultimately leading to formation of pores in e.g. bacterial membranes (terminal Membrane Attack Complex=MAC). C5a is generated when the complement system is activated in settings of inflammation and other immunological and inflammatory disorders/diseases.

Among the complement activation products, C5a is one of the most potent inflammatory peptides, with a broad spectrum of functions (Guo and Ward 2005). C5a exerts its effects through the high-affinity C5a receptors (C5aR and C5L2) (Ward 2009). C5aR belongs to the rhodopsin family of G-protein-coupled receptors with seven transmembrane segments; C5L2 has a similar structure but appears not to be G-protein-coupled. It is currently believed that C5a exerts its biological functions primarily through C5a-C5aR interaction, as few biological responses have been found for C5a-05L2 interaction. However, latest reports demonstrate signaling also through C5L2 activation (Rittirsch et al. 2008).

C5aR is widely expressed on myeloid cells including neutrophils, eosinophils, basophils, and monocytes, and non-myeloid cells in many organs, especially in the lung and liver, indicative of the importance of C5a/C5aR signaling. Widespread up-regulation of C5aR expression occurs during the onset of sepsis, and blockade of C5a/C5aR interaction by anti-05a, or anti-C5aR antibodies, or C5aR antagonists renders highly protective effects in rodent models of sepsis (Czermak et al. 1999; Huber-Lang et al. 2001; Riedemann et al. 2002).

C5a has a variety of biological functions (Guo and Ward 2005). C5a is a strong chemoattractant for neutrophils and also has chemotactic activity for monocytes and macrophages. C5a causes an oxidative burst (02 consumption) in neutrophils and enhances phagocytosis and release of granular enzymes. C5a has also been found to be a vasodilator. C5a has been shown to be involved in modulation of cytokine expression from various cell types and to enhance expression of adhesion molecule expression on neutrophils. High doses of C5a can lead to nonspecific chemotactic "desensitization" of neutrophils, thereby causing broad dysfunction. Many inflammatory diseases are attributable to the effects of C5a, including sepsis, acute lung injury, inflammatory bowel disease, rheumatoid arthritis and others. In the experimental setting of sepsis, exposure of neutrophils to C5a can lead to neutrophil dysfunction and paralysis of signaling pathways, leading to defective assembly of NADPH oxidase, paralysis of MAPK signaling cascades, a great depression of oxidative burst, phagocytosis and chemotaxis (Guo et al. 2006; Huber-Lang et al. 2002). Thymocytes apoptosis and delayed neutrophil apoptosis are two important pathogenic events for sepsis development, which are dependent on the presence of C5a. During experimental sepsis, C5a up-regulates β2-integrin expression on neutrophils to promote cell migration into organs, one of the major causes for multi-organ failure (MOF). It is also found that C5a is attributable to the activation of the coagulation pathway that occurs in experimental sepsis. C5a stimulates the synthesis and release from human leukocytes of pro-inflammatory cytokines such as TNF-α, IL-1β, IL-6, IL-8, and macrophage migration inhibitory factor (MIF). Given that complement activation is an event occurring during the onset of acute inflammation, C5a may come into play before emergence of most of the inflammatory "cytokine storm". It appears that C5a plays a key role in orchestrating and amplifying the performance of the cytokine network and the formation of systemic inflammatory response syndrome (SIRS).

In the immunological regulatory network tailing to the adaptive immunity, C5a affects the crosstalk between dendritic cells (DC) and γδ T cells, and this may result in a large production of inflammatory mediators such as IL-17 (Xu et al. 2010). An essential role for C5a has been established and defined in the generation of pathogenic Th17 responses in systemic lupus erythematosus (SLE) (Pawaria et al. 2014). In addition, it has been reported that C5a is a key regulator for Treg cells offering a powerful suppressive effect for Treg propagation and induction (Strainic et al. 2013). Given the fact that Treg and TH17 are the essential players in the autoimmune disease setting, inhibition of C5a signaling would be expected to significantly reduce overactive immune status in the autoimmune diseases.

IFX-1

IFX-1 is a chimeric monoclonal IgG4 antibody which specifically binds to the soluble human complement split product C5a. IFX-1 is composed of 1328 amino acids and has an approximate molecular weight of 148,472 Daltons. The CDR and FR sequences of IFX-1 are disclosed in Table 3 of WO 2015/140304 A1, also published as US 2017/0137499 A1. The contents of WO 2015/140304 A1 and US 2017/0137499 A1 are hereby incorporated by reference in their entirety.

IFX-1 is expressed in a mammalian CHO cell line as recombinant protein and finally formulated in a phosphate buffered saline solution (PBS+0.05% polysorbate 80) for intravenous administration. The binding of this antibody to human C5a facilitates a highly effective blockade of C5a-induced biological effects by disabling C5a binding to and reacting with its corresponding cell-bound receptors.

Various nonclinical studies were conducted to assess pharmacological and toxicological aspects of IFX-1, which can be divided into in vitro/ex vivo tests and in vivo studies including GLP toxicology studies in cynomolgus monkey (using IFX-1). None of the conducted nonclinical tests and studies revealed any toxicological or safety concerns for IFX-1. Human Phase I trial indicated that safety laboratory parameters, vital signs and ECG parameters showed no clinically relevant time- or dose-related changes.

In vitro analysis of IFX-1 demonstrates a strong binding capacity to soluble human C5a as well as a high blocking activity of C5a-induced biological effects such as lysozyme release from human neutrophils or CD11b up-regulation in neutrophils in human whole blood. One IFX-1 antibody reaches the capability of neutralizing the effects of 2 molecules C5a with close to 100% efficiency in experimental in vitro settings. Clinical trials with IFX-1 have been ongoing to test its clinical efficacy in several inflammatory diseases.

Technical Problems Underlying the Present Invention

Antibodies that specifically bind to the C5a part but not to the C5b part of C5 have been described in the prior art (Klos et al. (1998) J. Immunol. Meth. 111: 241-252; WO 01/15731; WO 03/015819). Previously generated anti-C5a antibodies exhibited only moderate blocking activities on biological effects induced by C5a. In consequence, anti-C5a antibodies of the prior art were either not capable of achieving a complete blockade of C5a-induced biological effects or had to be used in superstoichiometric amounts to reach a reasonably high blockage of C5a activity. The inventors succeeded in producing two monoclonal anti-C5a antibodies (named INab308 and INab708) that exhibit a strong blocking activity to C5a-induced biological effects, even when employed in stoichiometric amounts, i.e. 0.5 mole of a bivalent antibody per mole of C5a (see WO 2011/063980 A1, the content of which is incorporated herein by reference). Based on monoclonal antibody INab308, the inventors developed chimeric antibody IFX-1, which exhibits the same strong blocking activity (see WO 2015/140304 A1, the content of which is incorporated herein by reference).

However, the two monoclonal antibodies INab308 and INab708 specifically described in WO 2011/063980 A1 are murine antibodies. Antibody IFX-1 described in WO 2015/140304 A1 is a chimeric antibody. Consequently, these antibodies may elicit unwanted immunological responses when administered to human beings.

Thus, in view of an intended clinical use in patients, there remained a need in the prior art for anti-C5a antibodies that more closely resemble human antibodies but still exhibit excellent blockage of C5a activity.

The present inventors have now succeeded in producing humanized anti-C5a antibodies that have greatly improved humanness as compared to the antibodies described in WO 2011/063980 A1 and WO 2015/140304 A1, while still maintaining the advantageous properties of the antibodies described in WO 2011/063980 A1 and WO 2015/140304 A1, namely exhibiting the same high blocking activity to C5a-induced biological effects without affecting the biological activities of C5b.

The above overview does not necessarily describe all problems solved by the present invention.

SUMMARY OF THE INVENTION

In a first aspect the present invention relates to an antibody or an antigen-binding fragment thereof comprising a heavy chain variable domain (VH) and a light chain variable domain (VL), wherein said VH domain comprises, essentially consists of, or consists of an amino acid sequence according to SEQ ID NO: 10 (QVQLVQSGAE VKKPGASVKV SCKASGYSFT TFWMDWVRQA PGQGLEWIGR IDPSDSESRL DQRFKDRVTM TVDKSTSTVY MELSSLRSED TAVYYCARGN DGYYGFAYWG QGTLVTVSS, VH4) or an amino acid sequence having at least 80% sequence identity with SEQ ID NO: 10, wherein said amino acid sequence having at least 80% sequence identity with SEQ ID NO: 10 comprises the CDR1H, CDR2H, and CDR3H sequences of SEQ ID NO: 20 to 22, respectively, and wherein said amino acid sequence having at least 80% sequence identity with SEQ ID NO: comprises a V at amino acid position 5, an E at amino acid position 10, a K at amino acid position 12, a K at amino acid position 13, an A at amino acid position 16, an A at amino acid position 40, and/or a T at the amino acid position 76, and wherein said VL domain comprises, essentially consists of, or consists of an amino acid sequence according to SEQ ID NO: 16 (DIQMTQSPSS LSASVGDRVT ITCKASQSVD YDGDSYMKWY QQKPGKAPKL LIYAASNLQS GVPSRFSGSG SGTDFTLTIS SLQPEDFATY YCQQSNEDPY TFGQGTKLEI K, Vκ4) or an amino acid sequence having at least 80% sequence identity with SEQ ID NO: 16, wherein said amino acid sequence having at least 80% sequence identity with SEQ ID NO: 16 comprises the CDR1L, CDR2L, CDR3L sequences of SEQ ID NO: 23 to 25, respectively, and wherein said amino acid sequence having at least 80% sequence identity with SEQ ID NO: 16 comprises an A at amino acid position 13, a V at amino acid position 15, a D at amino acid position 17, a V at amino acid position 19, a T at amino acid position 22, a K at amino acid position 46, an A at amino acid position 47, an S at amino acid position 64, a T at amino acid position 78, an S at amino acid position 80, an S at amino acid position 81, an L at amino acid position 82, a Q at amino acid position 83, an F at amino acid position 87, and/or a Q at amino acid position 104.

In a second aspect the present invention relates to an antibody or an antigen-binding fragment thereof comprising a heavy chain variable domain (VH) and a light chain variable domain (VL), wherein said VH domain comprises, essentially consists of, or consists of an amino acid sequence according to SEQ ID NO: 17 (QVQLVQSGX$^9$E X$^{11}$KKPGASVKX$^{20}$SCKAS-GYSFT TFWMDWVX$^{38}$QA PGQGLEWX$^{48}$GR IDPSDSESRL DQX$^{63}$FKDRX$^{68}$TX$^{70}$ TVDKSTSTVY MX$^{82}$LSSX$^{86}$X$^{87}$SED X$^{91}$AVYYCARGN DGYYGFAYWG QGTLVTVSS), wherein X$^9$ is A or P, X$^{11}$ is L or V, X$^{20}$ is I or V, X$^{38}$ is K or R, X$^{48}$ is I or M, X$^{63}$ is K or R, X$^{68}$ is A or V, X$^{79}$ is L or M, X$^{82}$ is E or Q, X$^{86}$ is L or P, X$^{87}$ is R or T, and X$^{91}$ is S or T, or an amino acid sequence according to SEQ ID NO: 17 having one, two or three amino acid substitutions, wherein said amino acid sequence having one, two or three amino acid substitutions comprises the CDR1H, CDR2H, CDR3H sequences of SEQ ID NO: 20 to 22, respectively, and wherein said VL domain comprises, essentially consists of, or consists of an amino acid sequence according to SEQ ID NO: 18 (DIX³X⁴TQSPX⁹S LX¹²ASVGDRVT ITCKASQSVD YDGDSYMKWY QQKPGKAPKL LIYAASNLQS GX⁶²PSRFSGSG SGTDFTLTIS SLQX⁸⁴EDFATY YCQQSNEDPY TFGQGTKLEI K), wherein X³ is V or Q, X⁴ is L or M, X⁹ is A or S, X¹² is A or S, X⁶² is I or V, and X⁸⁴ is E or P, or an amino acid sequence according to SEQ ID NO: 18 having one, two, three, four, five, six, or seven amino acid substitutions, wherein said amino acid sequence having one, two, three, four, five, six, or seven amino acid substitutions comprises the CDR1L, CDR2L, CDR3L sequences of SEQ ID NO: 23 to 25, respectively.

In a third aspect the present invention relates to a pharmaceutical composition comprising:

the antibody or antigen-binding fragment thereof according to the first aspect or the antibody or antigen-binding fragment thereof according to the second aspect; and further comprising one or more pharmaceutically acceptable carriers, diluents, excipients, fillers, binders, lubricants, glidants, disintegrants, adsorbents, and/or preservatives.

In a fourth aspect the present invention relates to the antibody or antigen-binding fragment thereof according to the first aspect or the antibody or antigen-binding fragment thereof according to the second aspect for use in medicine.

In a fifth aspect the present invention relates to the antibody or antigen-binding fragment thereof according to the first aspect or the antibody or antigen-binding fragment thereof according to the second aspect for use in the treatment or prevention of a disease or disorder involving pathological C5a activity.

This summary of the invention does not necessarily describe all features of the present invention. Other embodiments will become apparent from a review of the ensuing detailed description.

DETAILED DESCRIPTION OF THE INVENTION

Definitions

Figure 1:
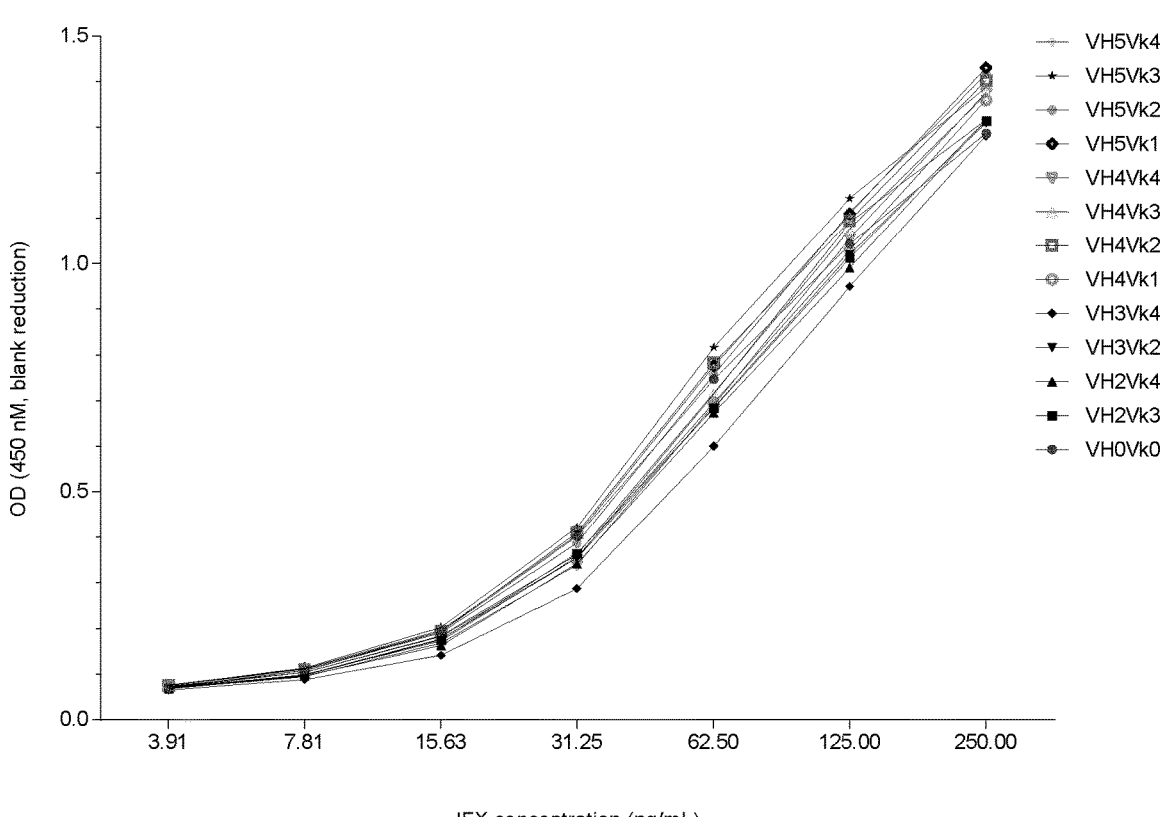
FIG. 1. Binding of IFX clones to rhC5a at different concentrations in a comparable dose-dependent manner. The parent molecule IFX-1 was marked as VH0Vk0.

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

Preferably, the terms used herein are defined as described in "A multilingual glossary of biotechnological terms: (IU-PAC Recommendations)", Leuenberger, H. G. W, Nagel, B. and Kölbl, H. eds. (1995), Helvetica Chimica Acta, CH-4010 Basel, Switzerland). Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Several documents (for example: patents, patent applications, scientific publications, manufacturer's specifications, instructions, GenBank Accession Number sequence submissions etc.) are cited throughout the text of this specification. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

Sequences: All sequences referred to herein are disclosed in the attached sequence listing that, with its whole content and disclosure, is a part of this specification.

As used herein, "human C5a" refers to the following 74 amino acid peptide: TLQKKIEEIA AKYKHSVVKK CCYDGACVNN DETCEQRAAR ISLGPRCIKA FTECCVVASQ LRANISHKDM QLGR (SEQ ID NO: 1). The amino acid sequence of human C5 can be found under the accession number UniProtKB P01031 (CO5_HUMAN). The terms "human C5a" and "hC5a" are used interchangeably herein.

As used herein, a first compound (e.g. an antibody) is considered to "bind" to a second compound (e.g. an antigen, such as a target protein), if it has a dissociation constant $K_d$ to said second compound of 1 µM or less, preferably 900 nM or less, more preferably 800 nM or less, more preferably 700 nM or less, more preferably 600 nM or less, more preferably 500 nM or less, more preferably 400 nM or less, more preferably 300 nM or less, more preferably 200 nM or less, even more preferably 100 nM or less, even more preferably 90 nM or less, even more preferably 80 nM or less, even more preferably 70 nM or less, even more preferably 60 nM or less, even more preferably 50 nM or less, even more preferably 40 nM or less, even more preferably 30 nM or less, even more preferably 20 nM or less, even more preferably 10 nM or less, even more preferably 5 nM or less, even more preferably 4 nM or less, even more preferably 3 nM or less, even more preferably 2 nM or less, and even more preferably 1 nM or less.

The term "binding" according to the invention preferably relates to a specific binding. "Specific binding" means that a binding moiety (e.g. an antibody) binds stronger to a target such as an epitope for which it is specific compared to the binding to another target. A binding moiety binds stronger to a first target compared to a second target if it binds to the first target with a dissociation constant $(K_d)$ which is lower than the dissociation constant for the second target. Preferably the dissociation constant $(K_d)$ for the target to which the binding moiety binds specifically is more than 10-fold, preferably more than 20-fold, more preferably more than 50-fold, even more preferably more than 100-fold, 200-fold, 500-fold or 1000-fold lower than the dissociation constant ($K_d$) for the target to which the binding moiety does not bind specifically.

As used herein, the term "$K_d$" (usually measured in "mol/L", sometimes abbreviated as "M") is intended to refer to the dissociation equilibrium constant of the particular interaction between a binding moiety (e.g. an antibody or fragment thereof) and a target molecule (e.g. an antigen or epitope thereof).

Methods for determining binding affinities of compounds, i.e. for determining the dissociation constant $K_d$, are known to a person of ordinary skill in the art and can be selected for instance from the following methods known in the art: Surface Plasmon Resonance (SPR) based technology, Bio-layer interferometry (BLI), enzyme-linked immunosorbent assay (ELISA), flow cytometry, isothermal titration calorimetry (ITC), analytical ultracentrifugation, radioimmuno-assay (RIA or IRMA) and enhanced chemiluminescence (ECL). Typically, the dissociation constant $K_d$ is determined at 20° C., 25° C., 30° C., or 37° C. If not specifically indicated otherwise, the $K_d$ values recited herein are determined at 20° C. by SPR.

An "epitope", also known as antigenic determinant, is the part of a macromolecule that is recognized by the immune system, specifically by antibodies, B cells, or T cells. As used herein, an "epitope" is the part of a macromolecule capable of binding to a compound (e.g. an antibody or antigen-binding fragment thereof) as described herein. In this context, the term "binding" preferably relates to a specific binding. Epitopes usually consist of chemically active surface groupings of molecules such as amino acids or sugar side chains and usually have specific three-dimensional structural characteristics, as well as specific charge characteristics. Conformational and non-conformational epitopes can be distinguished in that the binding to the former but not the latter is lost in the presence of denaturing solvents.

As used herein, a "conformational epitope" refers to an epitope of a linear macromolecule (e.g. a polypeptide) that is formed by the three-dimensional structure of said macromolecule. In the context of the present application, a "conformational epitope" is a "discontinuous epitope", i.e. the conformational epitope on the macromolecule (e.g. a polypeptide) which is formed from at least two separate regions in the primary sequence of the macromolecule (e.g. the amino acid sequence of a polypeptide). In other words, an epitope is considered to be a "conformational epitope" in the context of the present invention, if the epitope consists of at least two separate regions in the primary sequence to which an antibody of the invention (or an antigen-binding fragment thereof) binds simultaneously, wherein these at least two separate regions are interrupted by one or more regions in the primary sequence to which an antibody of the invention (or an antigen-binding fragment thereof) does not bind. Preferably, such a "conformational epitope" is present on a polypeptide, and the two separate regions in the primary sequence are two separate amino acid sequences to which an antibody of the invention (or an antigen-binding fragment thereof) binds, wherein these at least two separate amino acid sequences are interrupted by one more amino acid sequences in the primary sequence to which an antibody of the invention (or an antigen-binding fragment thereof) does not bind. Preferably, the interrupting amino acid sequence is a contiguous amino acid sequence comprising two or more amino acids to which the antibody (or the antigen-binding fragment thereof) does not bind. The at least two separate amino acid sequences to which an antibody of the invention (or an antigen-binding fragment thereof) binds are not particularly limited with regard to their length. Such a separate amino acid sequence may consists of only one amino acid as long as the total number of amino acids within said at least two separate amino acid sequences is sufficiently large to effect specific binding between the antibody (or the antigen-binding fragment thereof) and the conformational epitope.

A "paratope" is the part of an antibody that binds to the epitope. In the context of the present invention, a "paratope" is the part of an anti-C5a antibody (or an antigen-binding fragment thereof) as described herein that binds to the epitope.

The term "antibody" typically refers to a glycoprotein comprising at least two heavy (H) chains and two light (L) chains inter-connected by disulfide bonds, or an antigen-binding portion thereof. The term "antibody" also includes all recombinant forms of antibodies, in particular of the antibodies described herein, e.g. antibodies expressed in prokaryotes, unglycosylated antibodies, antibodies expressed in eukaryotes (e.g. CHO cells), glycosylated antibodies, and any antigen-binding antibody fragments and derivatives as described below. Each heavy chain is comprised of a heavy chain variable region (abbreviated herein as VH or $V_H$) and a heavy chain constant region. Each light chain is comprised of a light chain variable region (abbreviated herein as VL or $V_L$) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding fragment" of an antibody (or simply "binding portion"), as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) Fab fragments, monovalent fragments consisting of the VL, VH, CL and CH domains; (ii) F(ab')$_2$ fragments, bivalent fragments comprising two Fab fragments linked by a disulfide bridge at the hinge region; (iii) Fd fragments consisting of the VH and CH1 domains; (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker. Furthermore, although the two domains of the Fv fragment, VL and VH, are coded by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding fragment" of an antibody.

A further example is a binding-domain immunoglobulin fusion protein comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those of skill in the art, and the fragments are screened for utility in the same manner as are intact antibodies. Further examples of "antigen-binding fragments" are so-called microantibodies, which are derived from single CDRs. For example, Heap et al., 2005, describe a 17 amino acid residue microantibody derived from the heavy chain CDR3 of an antibody directed against the gp120 envelope glycoprotein of HIV-1 (Heap C. J. et al. (2005) *Analysis of a 17-amino acid residue, virus-neutralizing microantibody*. J. Gen. Virol. 86:1791-1800). Other examples include small antibody mimetics comprising two or more CDR regions that are fused to each other, preferably by cognate framework regions. Such a small antibody mimetic comprising $V_H$ CDR1 and VL CDR3 linked by the cognate VII FR2 has been described by Qiu et al., 2007 (Qiu X.-Q. et al. (2007) *Small antibody mimetics comprising two complementary-determining regions and a framework region for tumor targeting*. Nature biotechnology 25(8):921-929).

Thus, the term "antibody or antigen-binding fragment thereof", as used herein, refers to immunoglobulin molecules and immunologically active portions of immunoglobulin molecules, i.e. molecules that contain an antigen-binding site that immunospecifically binds an antigen. In a broad sense, the term "antibody or antigen-binding fragment thereof" includes immunoglobulin molecules of any type (e.g., IgG, IgE, IgM, IgD, IgA and IgY). However, the preferred immunoglobulin molecules of the present invention are of the IgG type. Within the IgG type, the preferred immunoglobulin molecules of the present invention can be from any class or subclass (e.g., IgG1; IgG2, preferably IgG2a and IgG2b; IgG3; or IgG4).

Antibodies and antigen-binding fragments thereof usable in the invention may be from any animal origin including birds and mammals. Thus, antibodies or fragments thereof can be from human, chimpanzee, rodent (e.g. mouse, rat, guinea pig, or rabbit), chicken, turkey, pig, sheep, goat, camel, cow, horse, donkey, cat, or dog origin. For many applications, it is particularly preferred that antibodies are of human or murine origin. Antibodies suitable for use in the present invention include chimeric molecules in which an antibody constant region derived from one species, e.g. human, is combined with the antigen binding site derived from another species, e.g. mouse. In the most preferred embodiments of the invention, antibodies and the antigen-binding fragments thereof include humanized molecules in which the antigen-binding sites of an antibody derived from a non-human species (e.g. from mouse) are combined with constant and framework regions of human origin.

As exemplified herein, antibodies of the invention can be obtained directly from hybridomas which express the antibody, or can be cloned and recombinantly expressed in a host cell (e.g., a CHO cell, or a lymphocytic cell). Further examples of host cells are microorganisms, such as *E. coli*, and fungi, such as yeast. Alternatively, they can be produced recombinantly in a transgenic non-human animal or plant.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another species or class. Typically, the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human is less likely to elicit an immune response from a human subject when the antibodies are injected than would the constant region from a non-human source. However, the definition is not limited to this particular example.

The term "humanized antibody" refers to a molecule having an antigen-binding site that is substantially derived from an immunoglobulin from a non-human species, wherein the remaining immunoglobulin structure of the molecule is based upon the structure and/or sequence of a human immunoglobulin. The antigen-binding site may either comprise complete variable domains fused onto constant domains or only the complementarity determining regions (CDR) grafted onto appropriate framework regions in the variable domains. Antigen-binding sites may be wild-type or modified by one or more amino acid substitutions, e.g. modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

Different methods for humanizing antibodies are known to the skilled person, as reviewed by Almagro & Fransson, 2008, Frontiers in Bioscience, 13:1619-1633, the content of which is herein incorporated by reference in its entirety. The review article by Almagro & Fransson is briefly summarized in US 2012/0231008 A1 which is the national stage entry of international patent application WO 2011/063980 A1. The contents of US 2012/0231008 A1 and WO 2011/063980 A1 are herein incorporated by reference in their entirety.

As used herein, "human antibodies" include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). Human antibodies of the invention include antibodies isolated from human immunoglobulin libraries or from animals transgenic for one or more human immunoglobulins and that do not express endogenous immunoglobulins, as described for example in U.S. Pat. No. 5,939,598 by Kucherlapati & Jakobovits.

The term "monoclonal antibody" as used herein refers to a preparation of antibody molecules of single molecular composition. A monoclonal antibody displays a single binding specificity and affinity for a particular epitope. Typically, monoclonal antibodies are produced by a hybridoma which includes a B cell obtained from a non-human animal, e.g. mouse, fused to an immortalized cell.

The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g. from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "transfectoma", as used herein, includes recombinant eukaryotic host cells expressing an antibody, such as CHO cells, NS/0 cells, HEK293 cells, HEK293T cells, plant cells, or fungi, including yeast cells.

As used herein, a "heterologous antibody" is defined in relation to a transgenic organism producing such an antibody. This term refers to an antibody having an amino acid sequence or an encoding nucleic acid sequence corresponding to that found in an organism not consisting of the transgenic organism, and being generally derived from a species other than the transgenic organism.

As used herein, a "heterohybrid antibody" refers to an antibody having light and heavy chains of different organismal origins. For example, an antibody having a human heavy chain associated with a murine light chain is a heterohybrid antibody.

Thus, "antibodies and antigen-binding fragments thereof" generally include, but are not limited to, polyclonal, monoclonal, monovalent, bispecific, heteroconjugate, multispecific, recombinant, heterologous, heterohybrid, chimeric, humanized (in particular CDR-grafted), deimmunized, or human antibodies, Fab fragments, Fab' fragments, F(ab)$_2$ fragments, fragments produced by a Fab expression library, Fd, Fv, disulfide-linked Fvs (dsFv), single chain antibodies (e.g. scFv), diabodies or tetrabodies (Holliger P. et al. (1993) Proc. Natl. Acad. Sci. U.S.A. 90(14), 6444-6448), nanobodies (also known as single domain antibodies), anti-idiotypic (anti-Id) antibodies (including, e.g., anti-Id antibodies to antibodies of the invention), and epitope-binding fragments of any of the above.

The antibodies described herein are preferably isolated. An "isolated antibody" as used herein, is intended to refer to an antibody which is substantially free of other antibodies having different antigenic specificities; e.g., an isolated antibody that specifically binds to C5a is substantially free of antibodies that specifically bind antigens other than C5a. An isolated antibody that specifically binds to an epitope, isoform or variant of human C5a may, however, have cross-reactivity to other related antigens, e.g. from other species (e.g. C5a species homologs, such as rat C5a). Moreover, an isolated antibody may be substantially free of other cellular material and/or chemicals. As used herein, a "combination of isolated antibodies" relates to antibodies having different specificities and being combined in a well-defined composition.

The term "naturally occurring", as used herein, as applied to an object refers to the fact that an object can be found in nature. For example, a polypeptide or polynucleotide sequence that is present in an organism (including viruses) that can be isolated from a source in nature and which has not been intentionally modified by man in the laboratory is naturally occurring.

"Conservative substitutions" may be made, for instance, on the basis of similarity in polarity, charge, size, solubility, hydrophobicity, hydrophilicity, and/or the amphipathic nature of the amino acid residues involved. Amino acids can be grouped into the following six standard amino acid groups:

(1) hydrophobic: Met, Ala, Val, Leu, Ile;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro; and (6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt a-helices. Some preferred conservative substitutions within the above six groups are exchanges within the following sub-groups: (i) Ala, Val, Leu and Ile; (ii) Ser and Thr; (ii) Asn and Gln; (iv) Lys and Arg; and (v) Tyr and Phe. Given the known genetic code, and recombinant and synthetic DNA techniques, the skilled scientist can readily construct DNAs encoding the conservative amino acid variants.

As used herein, "non-conservative substitutions" or "non-conservative amino acid exchanges" are defined as exchanges of an amino acid by another amino acid listed in a different group of the six standard amino acid groups (1) to (6) shown above.

The similarity of nucleotide and amino acid sequences, i.e. the percentage of sequence identity, can be determined via sequence alignments. Such alignments can be carried out with several art-known algorithms, preferably with the mathematical algorithm of Karlin and Altschul (Karlin & Altschul (1993) Proc. Natl. Acad. Sci. USA 90: 5873-5877), with hmmalign (HMMER package) or with the CLUSTAL algorithm (Thompson, J. D., Higgins, D. G. & Gibson, T. J. (1994) Nucleic Acids Res. 22, 4673-80) or the CLUSTALW2 algorithm (Larkin M A, Blackshields G, Brown N P, Chenna R, McGettigan P A, McWilliam H, Valentin F, Wallace I M, Wilm A, Lopez R, Thompson J D, Gibson T J, Higgins D G. (2007). Clustal W and Clustal X version 2.0. Bioinformatics, 23, 2947-2948).

The grade of sequence identity (sequence matching) may be calculated using e.g. BLAST, BLAT or BlastZ (or BlastX). A similar algorithm is incorporated into the BLASTN and BLASTP programs of Altschul et al. (1990) J. Mol. Biol. 215: 403-410. BLAST protein searches are performed with the BLASTP program available e.g. on the web site: http://blast.ncbi.nlm.nih.gov/Blast.cgi? PROGRAM=blastp&BLAST_PROGRAMS=blastp&P AGE_TYPE=BlastSearch&SHOW_DEFAULTS=on& LINK_LOC=blasthome Preferred algorithm parameters used are the default parameters as they are set on the indicated web site: Expect threshold=10, word size=3, max matches in a query range=0, matrix=BLOSUM62, gap costs=Existence: 11 Extension: 1, compositional adjustments=conditional compositional score matrix adjustment together with the database of non-redundant protein sequences (nr).

To obtain gapped alignments for comparative purposes, Gapped BLAST is utilized as described in Altschul et al. (1997) Nucleic Acids Res. 25: 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:I54-I62) or Markov random fields.

When percentages of sequence identity are referred to in the present application, these percentages are calculated in relation to the full length of the indicated reference sequence, if not specifically indicated otherwise. For example, the statement "an amino acid sequence having at least 80% sequence identity to SEQ ID NO: XYZ" means that the sequence identity percentage is calculated in relation to the total length of SEQ ID NO: XYZ.

A "biological activity" as used herein, refers to any activity a polypeptide may exhibit, including without limitation: enzymatic activity; binding activity to another compound (e.g. binding to another polypeptide, in particular binding to a receptor, or binding to a nucleic acid); inhibitory activity (e.g. enzyme inhibitory activity); activating activity (e.g. enzyme-activating activity); or toxic effects. Regarding variants and derivatives of a polypeptide, it is not required that the variant or derivative exhibits such an activity to the same extent as the parent polypeptide. A variant is regarded as a variant within the context of the present application, if it exhibits the relevant activity to a degree of at least 10% (e.g. at least 20%, at least 30%, at least 40%, or at least 50%) of the activity of the parent polypeptide. Likewise, a derivative is regarded as a derivative within the context of the present application, if it exhibits the relevant biological activity to a degree of at least 10% of the activity of the parent polypeptide. A particularly relevant "biological activity" in the context of the present invention is a binding activity to the conformational epitope of human C5a formed by the amino acid sequences NDETCEQRA (SEQ ID NO: 2) and SHKDMQL (SEQ ID NO: 3). Preferably, the relevant "biological activity" in the context of the present invention is a binding activity to the conformational epitope of human C5a formed by the amino acid sequences DETCEQR (SEQ ID NO: 4) and HKDMQ (SEQ ID NO: 5). Even more preferably, the relevant "biological activity" in the context of the present invention is a binding activity to the conformational epitope of human C5a formed by the amino acid sequences DETCEQR (SEQ ID NO: 4) and KDM. Assays for determining binding activity are known to a person of ordinary skill in the art and include ELISA and surface plasmon resonance assays.

As used herein, a "patient" means any mammal or bird who may benefit from a treatment with an anti-C5a antibody described herein. Preferably, a "patient" is selected from the group consisting of laboratory animals (e.g. mouse or rat), domestic animals (including e.g. guinea pig, rabbit, chicken, turkey, pig, sheep, goat, camel, cow, horse, donkey, cat, or dog), or primates including monkeys (e.g. African green monkeys, chimpanzees, bonobos, gorillas) and human beings. It is particularly preferred that the "patient" is a human being. The terms "patient" and "subject to be treated" (or in short: "subject") are used interchangeably herein.

As used herein, "treat", "treating" or "treatment" of a disease or disorder means accomplishing one or more of the following: (a) reducing the severity and/or duration of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, "prevent", "preventing", "prevention", or "prophylaxis" of a disease or disorder means preventing that a disorder occurs in a subject for a certain amount of time. For example, if an antibody of the invention (or an antigen-binding fragment thereof) is administered to a subject with the aim of preventing a disease or disorder, said disease or disorder is prevented from occurring at least on the day of administration and preferably also on one or more days (e.g. on 1 to 30 days; or on 2 to 28 days; or on 3 to 21 days; or on 4 to 14 days; or on 5 to 10 days) following the day of administration.

As used herein, "administering" includes in vivo administration, as well as administration directly to tissue ex vivo, such as vein grafts.

A "pharmaceutical composition" according to the invention may be present in the form of a composition, wherein the different active ingredients and diluents and/or carriers are admixed with each other, or may take the form of a combined preparation, where the active ingredients are present in partially or totally distinct form. An example for such a combination or combined preparation is a kit-of-parts.

An "effective amount" is an amount of a therapeutic agent sufficient to achieve the intended purpose. The effective amount of a given therapeutic agent will vary with factors such as the nature of the agent, the route of administration, the size and species of the subject to receive the therapeutic agent, and the purpose of the administration. The effective amount in each individual case may be determined empirically by a skilled artisan according to established methods in the art.

If the context does not state otherwise, the term "active agent" refers to the antibodies of the invention and to the antigen-binding fragments of the invention. The terms "active agent" and "therapeutic agent" are used interchangeably herein.

As used herein, the term "adjunctive therapy" refers to a combination therapy, in which at least two different drugs are administered to the patient. These at least two different drugs can be formulated into one single pharmaceutical composition containing both drugs. Alternatively, each drug can be formulated into a separate pharmaceutical composition and the pharmaceutical compositions are separately administered (e.g. at different time-points and/or by different routes of administration) to the patient. In this latter alternative, the (at least) two different drugs can be provided in a kit-of-parts.

"Pharmaceutically acceptable" means approved by a regulatory agency of the Federal or a state government or listed in the U.S. Pharmacopeia or other generally recognized pharmacopeia for use in animals, and more particularly in humans.

The term "carrier", as used herein, refers to a diluent, adjuvant, excipient, or vehicle with which the therapeutic agent is administered. Such pharmaceutical carriers can be sterile liquids, such as saline solutions in water and oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc. Examples of suitable pharmaceutical carriers are described in "Remington: The Science and Practice of Pharmacy" 22$^{nd}$ edition, Loyd V. Allen Jr. et al. (eds.), Pharmaceutical Press, 2012. Such compositions will contain a therapeutically effective amount of the compound, preferably in purified form, together with a suitable amount of carrier so as to provide the form for proper administration to the patient. The formulation should suit the mode of administration.

Generally known and practiced methods in the fields of molecular biology, cell biology, protein chemistry and antibody techniques are fully described in the continuously updated publications "Molecular Cloning: A Laboratory Manual", (Sambrook et al., Cold Spring Harbor); "Current Protocols in Molecular Biology" (F. M. Ausubel et al. Eds., Wiley & Sons); "Current Protocols in Protein Science" (J. E. Colligan et al. eds., Wiley & Sons); "Current Protocols in Cell Biology" (J. S. Bonifacino et al., Wiley & Sons) and "Current Protocols in Immunology" (J. E. Colligan et al., Eds., Wiley & Sons). Known techniques relating to cell culture and media are described in "Large Scale Mammalian Cell Culture (D. Hu et al., Curr. Opin. Biotechnol. 8:148-153, 1997); "Serum free Media" (K. Kitano, Biotechnol. 17:73-106, 1991); and "Suspension Culture of Mammalian Cells" (J. R. Birch et al. Bioprocess Technol. 10:251-270, 1990).

Embodiments of the Invention

The present invention will now be further described. In the following passages different aspects of the invention are defined in more detail. Each aspect defined below may be combined with any other aspect or aspects unless clearly indicated to the contrary. In particular, any feature indicated as being preferred or advantageous may be combined with any other feature or features indicated as being preferred or advantageous.

In a first aspect the present invention is directed to an antibody or an antigen-binding fragment thereof comprising a heavy chain variable domain (VH) and a light chain variable domain (VL), wherein said VH domain comprises, essentially consists of, or consists of an amino acid sequence according to SEQ ID NO: 10 (QVQLVQSGAE VKKPGASVKV SCKASGYSFT TFWMDWVRQA PGQGLEWIGR IDPSDSESRL DQRFKDRVTM TVDKSTSTVY MELSSLRSED TAVYYCARGN DGYYGFAYWG QGTLVTVSS, VH4) or an amino acid sequence having at least 80% sequence identity (preferably at least 85%, more preferably at least 90%, more preferably at least 95%, more preferably at least 96%, more preferably at least 97%, even more preferably at least 98%, or most preferably at least 99% sequence identity) with SEQ ID NO: 10, wherein said amino acid sequence having at least 80% (at least 85%, at least 90%, at least 95%, at least 96%, at least 97%, at least 98%, or at least 99%) sequence identity with SEQ ID NO: 10 comprises the CDR1H, CDR2H, and CDR3H sequences of SEQ ID NO: 20 to 22, respectively, and wherein said amino acid sequence having at least 80% (at least 85%, at least 90%, at least 95%, at least 96%, at least 97%, at least 98%, or at least 99%) sequence identity with SEQ ID NO: 10 comprises a V at amino acid position 5, an E at amino acid position 10, a K at amino acid position 12, a K at amino acid position 13, an A at amino acid position 16, an A at amino acid position 40, and/or a T at the amino acid position 76, and wherein said VL domain comprises, essentially consists of, or consists of an amino acid sequence according to SEQ ID NO: 16 (DIQMTQSPSS LSASVGDRVT ITCKASQSVD YDGDSYMKWY QQKPGKAPKL LIYAASNLQS GVPSRFSGSG SGTDFTLTIS SLQPEDFATY YCQQSNEDPY TFGQGTKLEI K, Vκ4) or an amino acid sequence having at least 80% sequence identity (preferably at least 85%, more preferably at least 90%, more preferably at least 95%, more preferably at least 96%, more preferably at least 97%, even more preferably at least 98%, or most preferably at least 99% sequence identity) with SEQ ID NO: 16, wherein said amino acid sequence having at least 80% (at least 85%, at least 90%, at least 95%, at least 96%, at least 97%, at least 98%, or at least 99%) sequence identity with SEQ ID NO: 16 comprises the CDR1L, CDR2L, CDR3L sequences of SEQ ID NO: 23 to 25, respectively, and wherein said amino acid sequence having at least 80% (at least 85%, at least 90%, at least 95%, at least 96%, at least 97%, at least 98%, or at least 99%) sequence identity with SEQ ID NO: 16 comprises an A at amino acid position 13, a V at amino acid position 15, a D at amino acid position 17, a V at amino acid position 19, a T at amino acid position 22, a K at amino acid position 46, an A at amino acid position 47, an S at amino acid position 64, a T at amino acid position 78, an S at amino acid position 80, an S at amino acid position 81, an L at amino acid position 82, a Q at amino acid position 83, an F at amino acid position 87, and/or a Q at amino acid position 104.

In a preferred embodiment of the first aspect, the amino acid sequence having at least 80% (preferably at least 85%, more preferably at least 90%, more preferably at least 95%, more preferably at least 96%, more preferably at least 97%, even more preferably at least 98%, or most preferably at least 99%) sequence identity with SEQ ID NO: 10 comprises at least four (preferably at least 5, more preferably at least 6, most preferably 7) of the following seven amino acids at the indicated positions:

a V at amino acid position 5,
an E at amino acid position 10,
a K at amino acid position 12,
a K at amino acid position 13,
an A at amino acid position 16,
an A at amino acid position 40, or
a T at the amino acid position 76.

In a preferred embodiment of the first aspect, the amino acid sequence having at least 80% (preferably at least 85%, more preferably at least 90%, more preferably at least 95%, more preferably at least 96%, more preferably at least 97%, even more preferably at least 98%, or most preferably at least 99%) sequence identity with SEQ ID NO: 16 comprises at least eight (preferably at least 9, more preferably at least 10, more preferably at least 11, even more preferably at least 12, even more preferably at least 13, even more preferably at least 14, most preferably 15) of the following fifteen amino acids at the indicated positions:

an A at amino acid position 13,
a V at amino acid position 15,
a D at amino acid position 17,
a V at amino acid position 19,
a T at amino acid position 22,
a K at amino acid position 46,
an A at amino acid position 47,
an S at amino acid position 64,
a T at amino acid position 78,
an S at amino acid position 80,
an S at amino acid position 81,
an L at amino acid position 82,
a Q at amino acid position 83,
an F at amino acid position 87, or
a Q at amino acid position 104.

In a preferred embodiment of the first aspect, the amino acid sequence having at least 80% (preferably at least 85%, more preferably at least 90%, more preferably at least 95%, more preferably at least 96%, more preferably at least 97%, even more preferably at least 98%, or most preferably at least 99%) sequence identity with SEQ ID NO: 10 comprises at least four (preferably at least 5, more preferably at least 6, most preferably 7) of the following seven amino acids at the indicated positions:

a V at amino acid position 5,
an E at amino acid position 10,
a K at amino acid position 12,
a K at amino acid position 13,
an A at amino acid position 16,
an A at amino acid position 40, or
a T at the amino acid position 76;
and optionally comprises 1, 2, or 3 amino acid substitutions, preferably conservative substitutions, located at amino acid positions 1 to 4 or 6 to 9 of SEQ ID NO: 10;
and
the amino acid sequence having at least 80% (preferably at least 85%, more preferably at least 90%, more preferably at least 95%, more preferably at least 96%, more preferably at least 97%, even more preferably at least 98%, or most preferably at least 99%) sequence identity with SEQ ID NO: 16 comprises at least eight (preferably at least 9, more preferably at least 10, more preferably at least 11, even more preferably at least 12, even more preferably at least 13, even more preferably at least 14, most preferably 15) of the following fifteen amino acids at the indicated positions:

an A at amino acid position 13,
a V at amino acid position 15,
a D at amino acid position 17,
a V at amino acid position 19,
a T at amino acid position 22,
a K at amino acid position 46,
an A at amino acid position 47,
an S at amino acid position 64,
a T at amino acid position 78,
an S at amino acid position 80,
an S at amino acid position 81, an L at amino acid position 82,
a Q at amino acid position 83,
an F at amino acid position 87, or
a Q at amino acid position 104;
and optionally comprises 1, 2, or 3 amino acid substitutions, preferably conservative substitutions, located at amino acid positions 1 to 10 of SEQ ID NO: 16.

In a second aspect the present invention is directed to an antibody or an antigen-binding fragment thereof comprising a heavy chain variable domain (VH) and a light chain variable domain (VL),
wherein said VH domain comprises, essentially consists of, or consists of an amino acid sequence according to SEQ ID NO: 17 (QVQLVQSGX$^9$E X$^{11}$KKPGASVKX$^{20}$ SCK-ASGYSFT TFWMDWVX$^{38}$QA PGQGLEWX$^{48}$GR IDPSDSESRL DQX$^{63}$FKDRX$^{68}$TX$^{70}$ TVDKSTSTVY MX$^{82}$LSSX$^{86}$X$^{87}$SED X$^{91}$AVYYCARGN DGYYGFAYWG QGTLVTVSS), wherein X$^9$ is A or P, X$^{11}$ is L or V, X$^{20}$ is I or V, X$^{38}$ is K or R, X$^{48}$ is I or M, X$^{63}$ is K or R, X$^{68}$ is A or V, X$^{70}$ is L or M, X$^{82}$ is E or Q, X$^{86}$ is L or P, X$^{87}$ is R or T, and X$^{91}$ is S or T, or an amino acid sequence according to SEQ ID NO: 17 having one, two or three amino acid substitutions, wherein said amino acid sequence having one, two or three amino acid substitutions comprises the CDR1H, CDR2H, CDR3H sequences of SEQ ID NO: 20 to 22, respectively, and
wherein said VL domain comprises, essentially consists of, or consists of an amino acid sequence according to SEQ ID NO: 18 (DIX$^3$X$^4$TQSPX$^9$S LX$^{12}$ASVGDRVT ITCKASQSVD YDGDSYMKWY QQKPGKAPKL LIYAASNLQS GX$^{62}$PSRFSGSG SGTDFTLTIS SLQX$^{84}$EDFATY YCQQSNEDPY TFGQGTKLEI K), wherein X$^3$ is V or Q, X$^4$ is L or M, X$^9$ is A or S, X$^{12}$ is A or S, X$^{62}$ is I or V, and X$^{84}$ is E or P, or an amino acid sequence according to SEQ ID NO: 18 having one, two, three, four, five, six, or seven amino acid substitutions, wherein said amino acid sequence having one, two, three, four, five, six, or seven amino acid substitutions comprises the CDR1L, CDR2L, CDR3L sequences of SEQ ID NO: 23 to 25, respectively.

In an embodiment of the first or second aspect, the VH domain comprises, essentially consists of, or consists of an amino acid sequence selected from the group consisting of VH1 to VH5 (SEQ ID NO: 7 to 11); and/or the VL domain comprises, essentially consists of, or consists of an amino acid sequence selected from the group consisting of Vκ1 to Vκ4 (SEQ ID NO: 13 to 16).

In an embodiment of the first or second aspect, the antibody or the antigen-binding fragment thereof comprises:

a) a VH domain comprising, essentially consisting of, or consisting of an amino acid sequence of SEQ ID NO: 10 (VH4) and a VL domain comprising, essentially consisting of, or consisting of an amino acid sequence according to SEQ ID NO: 16 (Vκ4), or b) a VH domain comprising, essentially consisting of, or consisting of an amino acid sequence of SEQ ID NO: 11 (VH5) and a VL domain comprising, essentially consisting of, or consisting of an amino acid sequence according to SEQ ID NO: 15 (Vκ3).

In an embodiment of the first or second aspect, the antibody is a humanized antibody.

In an embodiment of the first or second aspect, the antibody or the antigen-binding fragment thereof further comprises a constant domain. In some embodiments of the first or second aspect, the constant domain comprises, essentially consists of, or consists of the amino acid sequence according to SEQ ID NO: 19 (IgG4 WT constant), wherein said amino acid sequence according to SEQ ID NO: 19 optionally comprises one or more of the following amino acid exchanges:

an amino acid exchange S108P;

the amino acid exchanges T130Q and M308L;

the amino acid exchanges M132Y, S134T, and T136E.

In an embodiment of the first or second aspect, the antigen-binding fragment of an antibody is selected from the group consisting of Fab fragments, Fab' fragments, F(ab')2 fragments, Fd fragments, Fv fragments, disulfide-linked Fvs (dsFv), single domain antibodies and single chain Fv (scFv) antibodies.

In an embodiment of the first or second aspect, the antibody or the antigen-binding fragment thereof exhibits one or more of the following properties:— said antibody or said antigen-binding fragment thereof has a binding constant to C5a with a $K_d$ value of 10 nM or less (e.g. 9 nM or less; 8 nM or less, 7 nM or less, 6 nM or less, 5 nM or less, 4 nM or less, 3 nM or less, or 2 nM or less);

said antibody or said antigen-binding fragment thereof exhibits at least 75% blocking activity for biological effects induced by one molecule C5a;

said antibody or said antigen-binding fragment thereof does not inhibit CH50 activity in human plasma;

said antibody or said antigen-binding fragment thereof is capable of reducing *E. coli* induced IL-8 production in human whole blood.

said antibody or said antigen-binding fragment thereof has a reduced immunogenicity as compared to IFX-1.

A method for determining relative immunogenicity is shown in the examples below, i.e. an ADA screening assay. The abbreviation ADA refers to anti-drug antibodies.

In an embodiment of the first or second aspect, the antibody or antigen-binding fragment thereof binds to a conformational epitope formed by amino acid sequences NDETCEQRA (SEQ ID NO: 2) and SHKDMQL (SEQ ID NO: 3) of C5a, wherein the antibody or antigen-binding fragment thereof binds to at least one amino acid within the amino acid sequence according to SEQ ID NO: 2 and to at least one amino acid within the amino acid sequence according to SEQ ID NO: 3.

In a further embodiment of the first or second aspect, the antibody or antigen-binding fragment thereof binds to a conformational epitope formed by amino acid sequences DETCEQR (SEQ ID NO: 4) and HKDMQ (SEQ ID NO: 5) of C5a, wherein the antibody or antigen-binding fragment thereof binds to at least one amino acid within the amino acid sequence according to SEQ ID NO: 4 and to at least one amino acid within the amino acid sequence according to SEQ ID NO: 5.

In a further embodiment of the first or second aspect, the antibody or antigen-binding fragment thereof binds to a conformational epitope formed by amino acid sequences DETCEQR (SEQ ID NO: 4) and KDM of C5a, wherein the antibody or antigen-binding fragment thereof binds to at least one amino acid within the amino acid sequence according to SEQ ID NO: 4 and to at least one amino acid within the amino acid sequence according to KDM.

In a third aspect the present invention is directed to a pharmaceutical composition comprising:

the antibody or antigen-binding fragment thereof according to the first aspect or the antibody or antigen-binding fragment thereof according to the second aspect; and further comprising one or more pharmaceutically acceptable carriers, diluents, excipients, fillers, binders, lubricants, glidants, disintegrants, adsorbents, and/or preservatives.

In a fourth aspect the present invention is directed to the antibody or antigen-binding fragment thereof according to the first aspect or the antibody or antigen-binding fragment thereof according to the second aspect for use in medicine.

In a fifth aspect the present invention is directed to the antibody or antigen-binding fragment thereof according to the first aspect or the antibody or antigen-binding fragment thereof according to the second aspect for use in the treatment or prevention of a disease or disorder involving pathological C5a activity.

In an embodiment of the fifth aspect, the disease or disorder is selected from the group consisting of autoimmune disorders, inflammatory disorders, auto-inflammatory disorders, or related conditions, cardiovascular or cerebrovascular disorders, bacterial or viral infections, neurodegenerative disorders or related diseases, and cancers or precancerous conditions.

In some embodiments of the fifth aspect, the viral infection is HIV or AIDS.

EXAMPLES

The following examples are put forth so as to provide those of ordinary skill in the art with a complete disclosure and description of how to make and use the compounds, compositions and methods of the invention, and are not intended to limit the scope of what the inventors regard as their invention. Efforts have been made to ensure accuracy with respect to numbers used but some experimental errors and deviations should be accounted for. Unless indicated otherwise, molecular weight is average molecular weight, temperature is in degrees centigrade, and pressure is at or near atmospheric.

Example 1: Generation of Fully Humanized Anti-C5a Antibodies (IFX-2 Clones) Derived from IFX-1

This example details work in which the V region gene sequences encoding the chimeric antibody IFX-1 (VH0/Vκ0) were used to construct a series of fully humanized antibodies using Composite Human Antibody™ technology. The designed variable region genes of heavy chain and light chain were respectively cloned into vectors encoding a human IgG4 heavy chain constant domain (see SEQ ID NO: 19 but with an S108P amino acid exchange) and a human kappa light chain constant domain. In other publications, the S108P amino exchange is sometimes referred to as an S241P amino acid exchange (using Kabat numbering of a full-length human IgG4). Chimeric and humanized antibodies were transiently expressed in HEK EBNA cells and Protein A purified.

Methods and Results

Design of Composite Human Antibody™ Variable Region Sequences

Structural models of the IFX-1 antibody V regions were produced using Swiss PDB and analyzed in order to identify important "constraining" amino acids in the V regions that were likely to be essential for the binding properties of the antibody. Most residues contained within the CDRs together with a number of framework residues were considered to be important. The VH and Vκ sequences of IFX-1 contain typical framework residues and the CDR 1, 2 and 3 motifs are comparable to many murine antibodies.

From the above analysis, it was considered that composite human sequences of IFX-1 could be created with a wide latitude for alternative residues outside of the CDRs but with only a narrow menu of possible residues within the CDR sequences. Preliminary analysis indicated that corresponding sequence segments from several human antibodies could be combined to create CDRs similar or identical to those in the murine sequences. For regions outside of, and flanking the CDRs, a wide selection of human sequence segments were identified as possible components of the novel humanized V regions.

CD4+ T Cell Epitope Avoidance

Based upon the structural analysis, a large preliminary set of sequence segments that could be used to create IFX-1 humanized variants were selected and analyzed using iTope™ technology for in silico analysis of peptide binding to human MHC class II alleles (Perry et al *New Approaches to Prediction of Immune Responses to Therapeutic Proteins during Preclinical Development* (2008). Drugs R D 9 (6): 385-396), and using the TCED™ of known antibody sequence-related T cell epitopes (Bryson et al *Prediction of Immunogenicity of Therapeutic Proteins* (2010). Biodrugs 24 (1):1-8). Sequence segments that were identified as significant non-human germline binders to human MHC class II or that scored significant hits against the TCED™ were discarded. This resulted in a reduced set of segments, and combinations of these were again analyzed, as above, to ensure that the junctions between segments did not contain potential T cell epitopes. Selected sequence segments were assembled into complete V region sequences that were devoid of significant T cell epitopes. Five heavy chain (VH1 to VH5) and four light chain (Vκ1 to Vκ4) sequences were then chosen for gene synthesis and expression in mammalian cells. The amino acid sequences of VH1 to VH5 are shown in the sequence listing as SEQ ID NOs: 7 to 11, respectively. The amino acid sequences of Vκ1 to Vκ4 are shown in the sequence listing as SEQ ID NOs: 13 to 16, respectively.

Construction of Chimeric Antibody and Humanised Variants

The VH and Vκ sequences of IFX-1 (VH0 (SEQ ID NO: 6) and Vκ0 (SEQ ID NO: 12)) and its humanized variants were synthesized with flanking restriction enzyme sites for cloning into Abzena's pANT expression vector system for human IgG4 (S241P) heavy chain and kappa light chain, respectively. The VH regions were cloned between the Mlu I and Hind III restriction sites, and the Vκ regions were cloned between the BssH II and BamH I restriction sites. All constructs were confirmed by sequencing.

Expression and Purification of Antibodies

Chimeric IFX-1 (VH0/Vκ0), two control antibodies (VH0/Vκ1, VH1/Vκ0) and combinations of composite IgG4 (S241P) VH and Vκ chains (a total of 23 pairings, Table 1) were transiently transfected into HEK EBNA adherent cells (LGC Standards, Teddington, UK) using a PEI transfection method and incubated for seven days post-transfection.

Supernatant antibody titres were determined by ELISA, and it was observed that VH1 containing variants showed consistently poorer expression when compared to other variants (data not shown).

TABLE 1

Summary table of the antibodies produced by transient transfection (crossed boxes) including a chimeric (VH0/Vκ0), two control humanized variants (VH1/Vκ0 and VH0/Vκ1) and 20 IFX-1 Composite Human Antibody ™ variants.

| | VH0 | VH1 | VH2 | VH3 | VH4 | VH5 |
|---|---|---|---|---|---|---|
| Vκ0 | X | X | | | | |
| Vκ1 | X | X | X | X | X | X |
| Vκ2 | | X | X | X | X | X |
| Vκ3 | | X | X | X | X | X |
| Vκ4 | | X | X | X | X | X |

Antibodies (excluding poorly expressing VH1 variants) were purified from cell culture supernatants on Protein A sepharose columns (GE Healthcare, Little Chalfont, UK), buffer exchanged into 1×PBS pH 7.2 and quantified by $OD_{280nm}$ using an extinction coefficient ($Ec_{(0.1\%)}$) based on the predicted amino acid sequence. Antibodies were analyzed using SDS-PAGE by loading 1 μg of each antibody on the gel and bands corresponding to the profile of a typical antibody were observed (data not shown).

Example 2: Comparison of Different IFX-2 Clones to Parent Antibody IFX-1

Materials and Reagents

For CD11b assay:

ACD, Sigma Aldrich (Taufkirchen, Germany), Cat. No. C3821-50ML reagents for flow cytometer (all BD Bioscience, NJ, USA)

FACS Flow Sheat Fluid, Cat. No. 342003

FACS Shutdown solution, Cat. No. 334224

FACS Clean solution, Cat. No. 340345 rat anti-mouse CD11b:FITC, Cat. No. 553310, 0.5 mg/mL

10× lysing solution, BD Bioscience (NJ, USA), Cat. No. 349202→1:10 diluted in AnalaR water HBSS, Life Technologies GmbH (Darmstadt, Germany), Cat. No. 14025-050

FBS, Invitrogen (CA, USA), Cat. No. 10099133→heat-inactivation: 56° C., 30 min sodium azide, Merck (Darmstadt, Germany), Cat. No. 1.06688.0250 recombinant human C5a (rhC5a), Sigma Aldrich (Taufkirchen, Germany), Cat. No. C5788-.1MG, expressed in *E. coli*, purity: ~95%, dissolved in sterile AnalaR water staining buffer (SB-buffer): 1% heat-inactivated FBS+ 0.1% sodium azide in 1×PBS human blood (used immediately) from healthy donor containing 12% ACD For C5a-base PK ELISA:

AnalaR water, VWR International (Darmstadt, Germany), Cat. No. 102923C recombinant human C5a (rhC5a), Hycult Biotech (Uden, The Netherlands), Cat. No. HC2101, expressed in *E. coli*, dissolved in sterile AnalaR water rhC5a desarginine derivative (rhC5aDArg), Hycult Biotech (Uden, The Netherlands), Cat. No. HC2102, expressed in *E. coli*, dissolved in sterile AnalaR water IFX-1, anti-human C5a antibody applied as control, InflaRx (Jena, Germany), 10 mg/mL in PBS+0.05% Tween80 mouse anti-human IgG4:HRP, AbD Serotec (Puchheim, Germany), Cat. No. MCA2098P, 1 mg/mL $Na_2CO_3$, Sigma-Aldrich (Taufkirchen, Germany), Cat. No. 71350 (Sigma, WI, USA, Cat. No. 31432)

$NaHCO_3$, VWR International (Darmstadt, Germany), Cat. No. L1730

$NaN_3$, VWR International, (Darmstadt, Germany), Cat. No. 1.06688.0100

PBS powder, Sigma-Aldrich (Taufkirchen, Germany), Cat. No. P5368-10PAK 4 1 package dissolved in 1000 mL deionised water Tween 20, Sigma-Aldrich, (Taufkirchen, Germany), Cat. No. P1379-25ML BSA, Sigma-Aldrich (Taufkirchen, Germany), Cat. No. A7030-100G coating buffer: 1.59 g $Na_2CO_3$+2.93 g $NaHCO_3$+0.2 g $NaN_3$ in 1000 mL AnalaR water, pH 9.6 washing buffer: 1×PBS+0.05% Tween 20 assay diluent: 3% BSA in 1×PBS+0.05% Tween 20 (3% BSA/PBST)

TMB substrate (substrate solution C), BioLegend/Biozol (Heidelberg, Germany), Cat. No. BLD-78105 stop solution: sulfuric acid (Sigma-Aldrich, Cat. No. 258105-100ML) 1:10 diluted in AnalaR water For Plasma Hemolytic Activity (CH50):

AnalaR water, VWR International (Darmstadt, Germany), Cat. No. 102923C

Complement CH50 assay, Haemoscan (Groningen, Netherlands), Cat. No. K002

Healthy human plasma pool, huPP-013, in-house preparation

Methods rhC5a-Based ELISA

For the ELISA, 100 µL of rhC5a (1 µg/mL) was coated on a 96-well ELISA plate overnight at 4° C. Plate was washed (5×) and blocked with 200 µL of blocking buffer for 1 h at 37° C. Following the washing steps (5×), IFX clones in 2-fold serial dilution from 250 ng/mL-3.91 ng/mL were added to the C5a-coated wells. After the 2-h incubation at 37° C. and washing steps (5×), 0.04 µg/mL HRP-labeled anti-human IgG4 antibody was applied for 1 h at 37° C. to detect the bound IFX clones. For color development, 100 µL of TMB substrate was added after wash (5×) and incubated for 5 min at RT. Color reaction was stopped with 100 µL stop solution. Absorbance readout at 450 nm was performed within 30 min after color reaction using the plate reader. Blank reduction was performed with the raw data.

Plasma Hemolytic Activity (CH50)

The total hemolytic complement titer (CH50) is a conventional method to determine the activation of classical complement pathway. In brief, sheep red blood cells (sRBC) were prepared from fresh sheep whole blood by centrifugation and sensitized with an anti-sRBC antibody. Plasma samples from healthy volunteers containing IFX clones were serially diluted and incubated with the sensitized sRBC at 37° C. for 30 min. After incubation, the mixture was centrifuged, and the degree of hemolysis was quantified by measuring the absorbance of the hemoglobin released into the supernatant at 450 nm. The amount of complement activity was determined by examining the capacity of various dilutions of test plasma sample to lyse the sensitized sRBC.

CD11b Potency Assay

Human whole blood was stimulated with 16.7 nM rhC5a. To test the blocking activity of IFX-1 and IFX-2 clones on rhC5a-induced CD11b upregulation, the antibodies were diluted to the final concentration with Ag:Ab ratio of 1:1. Blood incubated with buffer alone (HBSS control) served as the non-stimulated condition to assess the baseline CD11b expression. Blood with IFX antibody alone was used to exclude the inhibitory or stimulatory effect of the antibody on human blood. The mixed samples were incubated at 37° C. for 20 min to induce C5a-mediated CD11b upregulation. Afterwards, a FITC-conjugated anti-mouse CD11b antibody was further incubated with the samples for 30 min on ice to stain the CD11b on the cell surface of granulocytes. The fluorescence signal was captured through Flow Cytometer.

Statistical Analysis

Graphs and statistical analysis were performed with GraphPad PRISM® V7.05.

Results

IFX-2 Clones Bound Equally Well to C5a in Comparison to IFX-1

To characterize the binding of IFX-2 clones to C5a, the rhC5a-based ELISA platform was employed. 12×IFX-2 and 1×IFX-1 (VH0Vk0) clones in range of 3.91 ng/mL-250 ng/mL were applied as samples to the 1 µg/mL rhC5a-coated 96-well plate. The C5a-captured IFX clones were then detected with 0.04 µg/mL of HRP-conjugated anti-human IgG4 mAb. The more IFX antibody bound to C5a, the stronger chemiluminescent signal would appear. As shown in FIG. 1, all tested antibodies in the applied concentration range bound to the coated rhC5a in a comparable dose-dependent manner.

A similar ELISA-based assay was performed in ABZENA to quantify the $EC_{50}$ of IFX clones on C5a binding. In the range of 0-100 ng/mL, all IFX clones showed a very close binding behavior to C5a. In comparison to the parent molecule IFX-1, the relative $EC_{50}$s of all IFX-2 clones were within the 2-fold range, the median value was 1.04 (Table 2).

TABLE 2

The relative $EC_{50}$ of IFX-2 to IFX-1 (VH0Vk0) on C5a binding affinity.

| Sample ID | Relative $EC_{50}$ |
|---|---|
| VH0Vk0 (IFX-1) | 1.00 |
| VH2Vk3 | 1.09 |
| VH2Vk4 | 0.99 |
| VH3Vk2 | 1.05 |
| VH3Vk4 | 0.86 |
| VH4Vk1 | 1.00 |
| VH4Vk2 | 0.86 |
| VH4Vk3 | 0.91 |
| VH4Vk4 | 1.03 |
| VH5Vk1 | 1.28 |
| VH5Vk2 | 1.05 |
| VH5Vk3 | 1.14 |
| VH5Vk4 | 1.53 |
| Median of IFX-2 clones | 1.04 |

IFX-2 Antibodies Showed No Inhibition on the Formation of Membrane Attack Complex (MAC)

The parent IFX-1 (VH0Vk0) is known to neutralize C5a without interfering with the C5 cleavage to C5a and C5b. C5b is the starting material of membrane attack complex C5b-9, which is the terminal product of classical complement pathway and forms pores in membranes. Total hemolytic complement titer (CH50) was used to index the activation of classical complement pathway via MAC-mediated hemolysis of sensitized sheep red blood cells (SRBC).

Pooled human plasma with an initial concentration of 100 µg/mL of respective IFX clones (12×IFX-2 and 1×IFX-1 (VH0Vk0)) was serially diluted to 4-, 8-, 16-, 32-, 64-, and 128-fold, and incubated with the erythrocyte suspension. The degree of hemolysis was quantified by measuring the absorbance of the hemoglobin released into the supernatant at 450 nm.

TABLE 3

CH50 (plasma dilution factor) of each test IFX clone.

| Sample ID | CH50 (DF, -fold) |
|---|---|
| VH0Vk0 (IFX-1) | 74.25 |
| VH2Vk3 | 72.62 |
| VH2Vk4 | 74.19 |
| VH3Vk2 | 76.71 |
| VH3Vk4 | 75.46 |
| VH4Vk1 | 75.69 |
| VH4Vk2 | 72.04 |
| VH4Vk3 | 70.47 |
| VH4Vk4 | 75.31 |
| VH5Vk1 | 71.20 |
| VH5Vk2 | 74.21 |
| VH5Vk3 | 73.24 |
| VH5Vk4 | 76.87 |
| Median of IFX-2 clones | 74.20 |

Figure 2:
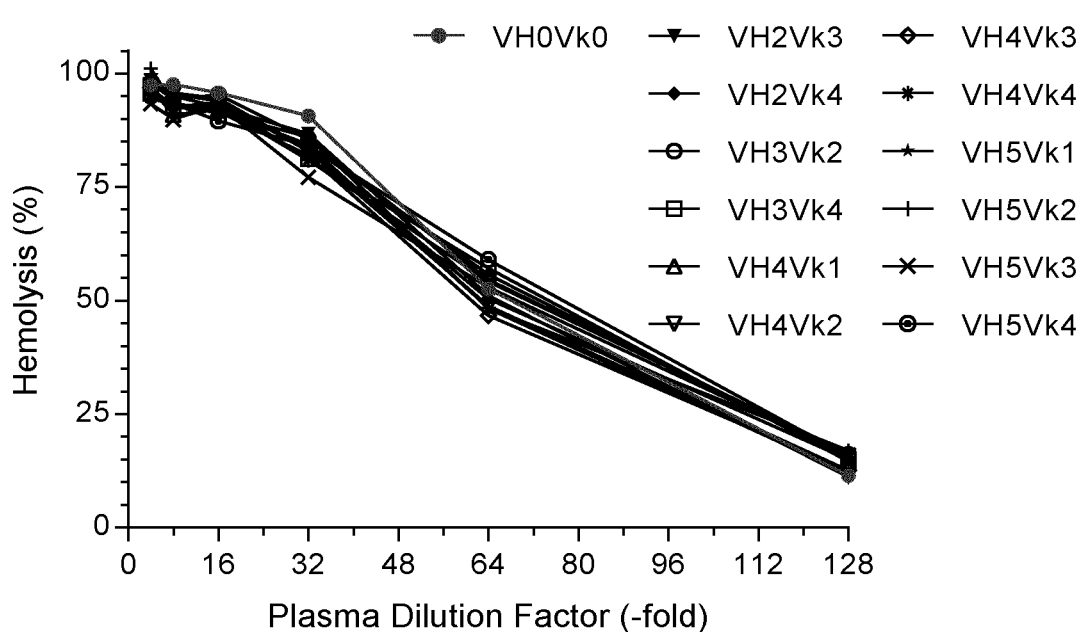
FIG. 2. Plotting of sample hemolysis (%) and plasma dilution factor (-fold) to calculate the CH50. The parent molecule IFX-1 was marked as VH0Vk0.

As shown in FIG. 2 and Table 3, a 70- to 77-fold (median 74-fold) dilution of the IFX-2 clones or a 74-fold dilution of the parent molecule IFX-1 were required to achieve the 50% hemolysis (CH50), which is fully comparable. It demonstrated that the mutations on IFX-2 clones did not impair the activation of classical complement pathway.

IFX-2 Antibodies Effectively Blocked the rhC5a-Driven CD11b Upregulation

Figure 3:
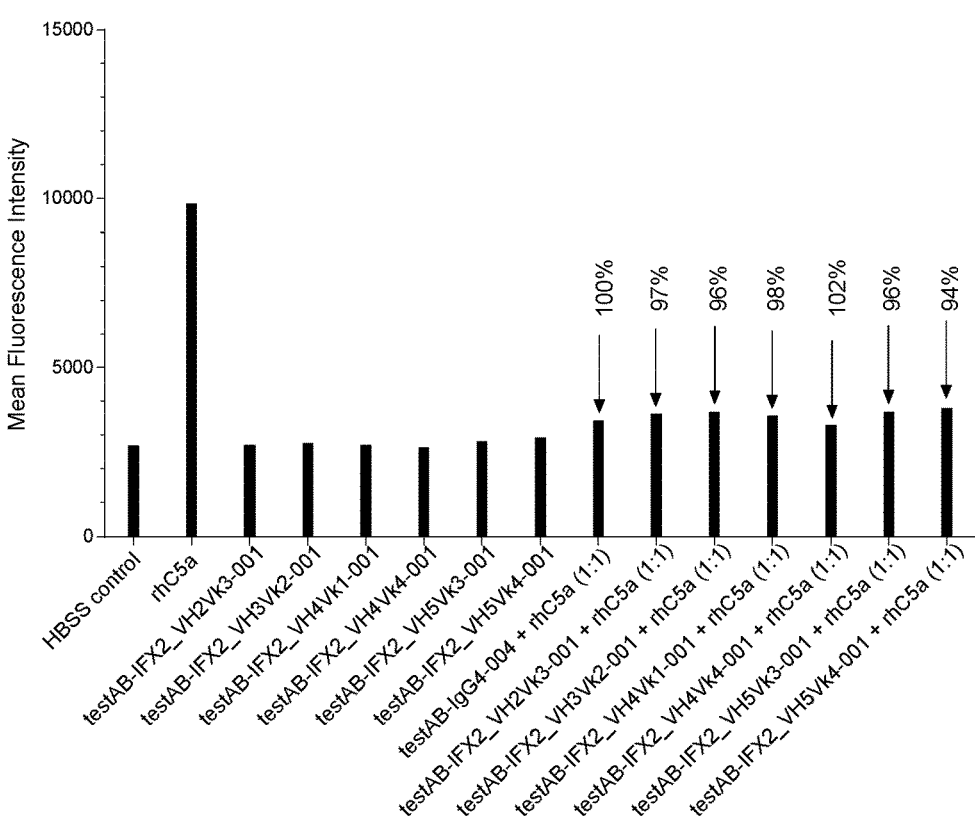
FIG. 3. Anaphylatoxin rhC5a induced-CD11b upregulation and its individual blockade by 12 IFX-2 clones at the Ag:Ab molar ratio of 1:1 in comparison to that by IFX-1 (testAB-IgG4-004).
Figure 3:
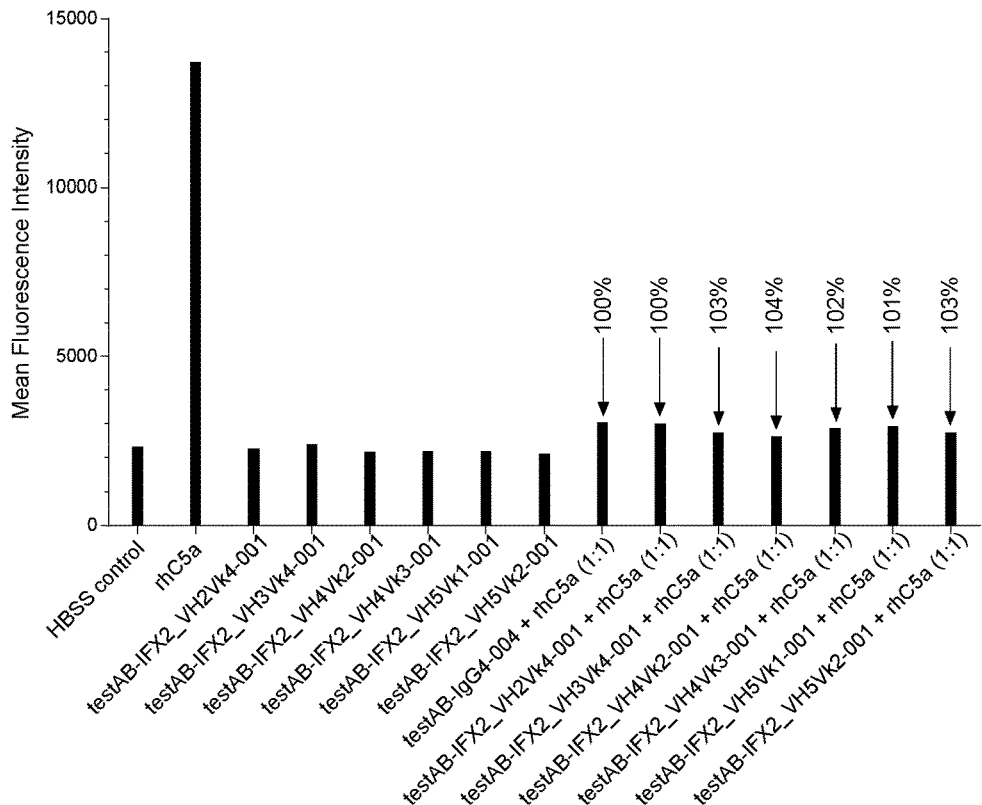

CD11b upregulation on the surface of human granulocytes is detectable within minutes after addition of rhC5a to human whole blood. CD11b levels were determined using fluorescence labeled anti-CD11b antibody and indicated as the mean fluorescence intensity (MFI). Blocking of the rhC5a-driven CD11b up-regulation was evaluated with 12×IFX-2 antibodies in comparison to IFX-1 in two CD11b potency assays. In both assays, 16.7 nM rhC5a was used as the stimulus, which respectively induced 3.65- and 5.89-fold upregulation of CD11b expression. All IFX clones were tested in a 1:1 molar ratio for the blockade on CD11b upregulation. The blocking activity of IFX clones were calculated according to the respective fluorescence intensity change to the rhC5a-stimulated condition. The activity of parent molecule IFX-1 was set to be 100%. At the rhC5a: IFX clone ratio of 1:1, IFX-2 clones showed 94%-104% of relative blocking activity (see FIG. 3). The median relative blocking activities of IFX-2 clones was 100.68%.

Example 3: ADA Analysis in Non-Human Primate after IFX-1/IFX-2 Treatment

Materials and Reagents

TABLE 4

Reagents and their suppliers.

| precursors | Supplier | Product-Number |
|---|---|---|
| AnalaR water | VWR International | 102923C |
| Avidin-HRP | Biolegend | 405103 |
| Solution C (TMB) | Biolegend | 78105 |
| Rabbit anti-CaCP29-IgG4 pAB | Charles River | n/a |

TABLE 4-continued

Reagents and their suppliers.

| precursors | Supplier | Product-Number |
|---|---|---|
| IFX-1 | InflaRx | n/a |
| IFX-2 | InflaRx | n/a |
| Blocking Buffer I | AppliChem | A7099.0500 |
| Cross Down Buffer | AppliChem | A6485.0500 |
| Monkey serum | LPT Hamburg | n.a. |
| PBS powder | Sigma-Aldrich | P5368-10PAK |
| Sodium azide NaN$_3$ | VWR International | 1.06688.0100 |
| Sodium bicarbonate NaHCO3 | VWR International | L1703 |
| Sodium carbonate Na$_2$CO$_3$ | Honeywell | 31432-250G |
| Sulfuric acid H$_2$SO$_4$ | VWR International | 258105-100ML |
| Tween20 | Sigma-Aldrich | P1379-25ML |

Method

Anti-drug antibodies are determined in a two-step approach. Serum samples are screened for anti-drug antibodies within the ADA screening ELISA. A fixed assay cut-point based on optical density (OD) is 0.102 (according to ADA screening ELISA validation with human plasma for detection of IFX-1 ADA), and should result in 9% false positive samples. Therefore, samples obtained positive in the ADA screening ELISA must be analyzed within the ADA confirmatory ELISA to confirm or reject the results and to determine the ADA concentration, if applicable.

The ADA screening ELISA is a bridging ELISA employing the drug IFX-1 (anti-human C5a antibody) as capture antibody (non-labeled) and detection antibody (biotin-labeled). The anti-drug antibodies used for the preparation of calibration (CAL) curve and spiking of quality control (QC) samples were purified from rabbit serum after immunization of the rabbit with purified IFX-1. As the anti-drug antibodies have two binding sites, they can bind (bridge) both, the capture IFX-1 as well as the labeled IFX-1 used for detection. All plasma samples screened ADA-positive are re-evaluated in the ADA confirmatory ELISA which is based on the ADA screening ELISA setup. Additional free unlabeled drug (IFX-1) is added to the samples to compete the binding of potential anti-drug antibodies to the captured IFX-1 on the plate. If there are anti-drug antibodies available, they would bind to the added free unlabeled IFX-1 and would therefore be indetectable. If a drug-specific ADA inhibition is observed and the screening result is confirmed, the sample is considered to be confirmed positive.

ADA screening ELISA and ADA confirmatory ELISA were carried out as described in the following:

Briefly, 100 µl/well capture antibody (IFX-1, 0.5 µg/ml) is incubated over night at 5±3° C. on high binding plates. After a washing step, 200 µl blocking buffer is pipetted into each well and the plate is incubated for 2 hours at 37° C.±2° C. After another washing step, 100 µl/well CAL samples, QC samples and samples of interest (test samples) are pipetted into the wells and incubated for 2 hours at 37° C.±2° C. Following a washing step, 100 µl of detection antibody (biotinylated IFX-1, 0.08 µg/ml) is pipetted into each well for an incubation of 60 minutes at 37° C.±2° C. The plates are washed thereafter and 100 µl diluted Avidin-HRP (1:3000) is added to each well and incubated for 30 minutes at 37° C.±2° C. After a final washing step, 100 µl/well TMB (substrate solution) is added, incubated for 5 minutes at RT protected from light, and the reaction is stopped by adding 100 µl/well of diluted sulfuric acid. The color intensity is analyzed at 450 nm with the Tecan Infinite M200 reader using Magellan™ 6.5 software.

Plasma samples with unknown ADA concentrations are diluted 1:2 in CrossDown buffer before analyzed in ADA screening ELISA. For re-evaluation in the ADA confirmatory ELISA, samples are diluted 1:2 once in CrossDown buffer and once in drug-spiked CrossDown buffer (IFX-1 concentration 100 μg/ml).

Samples with an OD value below 0.102 in the ADA screening assay are classified as "negative". Samples with a signal blocking of more than 50% in the ADA confirmatory assay are classified as "confirmed positive". Results are shown in Table 5:

Result

The IFX-2 treated animals did not develop detectable ADA 8 weeks after administration.

TABLE 5

| Summary of ADA screening and confirmatory ELISA | | | | | |
|---|---|---|---|---|---|
| IFX-1 treated animals | | | IFX-2 treated animals | | |
| animal ID (timepoint) | ADA screening | ADA confirmatory | animal ID (timepoint) | ADA screening | ADA confirmatory |
| #1 (pre) | negative | not applicable | #13 (pre) | negative | not applicable |
| #1 (TD 57) | negative | not applicable | #13 (TD 57) | negative | not applicable |
| #2 (pre) | negative | not applicable | #14 (pre) | negative | not applicable |
| #2 (TD 57) | potential positive | confirmed positive | #14 (TD 57) | negative | not applicable |
| #3 (pre) | negative | not applicable | #15 (pre) | negative | not applicable |
| #3 (TD 57) | negative | not applicable | #15 (TD 57) | negative | not applicable |
| #4 (pre) | negative | not applicable | #16 (pre) | negative | not applicable |
| #4 (TD 57) | potential positive | confirmed positive | #16 (TD 57) | negative | not applicable |
| #5 (pre) | negative | not applicable | #17 (pre) | negative | not applicable |
| #5 (TD 57) | negative | not applicable | #17 (TD 57) | negative | not applicable |
| #6 (pre) | negative | not applicable | #18 (pre) | negative | not applicable |
| #6 (TD 57) | negative | not applicable | #18 (TD 57) | negative | not applicable |

Sequence Listing Free Text Information

SEQ ID NO: 6 VH0
SEQ ID NO: 7 VH1
SEQ ID NO: 8 VH2
SEQ ID NO: 9 VH3
SEQ ID NO: 10 VH4
SEQ ID NO: 11 VH5
SEQ ID NO: 12 V_kappa_0
SEQ ID NO: 13 V_kappa_1
SEQ ID NO: 14 V_kappa_2
SEQ ID NO: 15 V_kappa_3
SEQ ID NO: 16 V_kappa_4
SEQ ID NO: 17 Consensus sequence formed from the combination of VH1 to VH5
SEQ ID NO: 18 Consensus sequence formed from the combination of V_kappa_1 to V_kappa_4
SEQ ID NO: 20 IFX-1 CDR1 heavy chain
SEQ ID NO: 21 IFX-1 CDR2 heavy chain
SEQ ID NO: 22 IFX-1 CDR3 heavy chain
SEQ ID NO: 23 IFX-1 CDR1 light chain
SEQ ID NO: 24 IFX-1 CDR2 light chain
SEQ ID NO: 25 IFX-1 CDR3 light chain

The invention claimed is:

1. An antibody or an antigen-binding fragment thereof that specifically binds to human C5, comprising a heavy chain variable domain (VH) and a light chain variable domain (VL), a) wherein said VH domain comprises or consists of the amino acid sequence according to SEQ ID NO: 8 (VH2) and the VL domain comprises or consists of the amino acid sequence according to SEQ ID NO: 15 (Vκ3);

b) wherein said VH domain comprises or consists of the amino acid sequence according to SEQ ID NO: 8 (VH2) and the VL domain comprises or consists of the amino acid sequence according to SEQ ID NO: 16 (Vκ4);

c) wherein said VH domain comprises or consists of the amino acid sequence according to SEQ ID NO: 9 (VH3) and the VL domain comprises or consists of the amino acid sequence according to SEQ ID NO: 14 (Vκ2);

d) wherein said VH domain comprises or consists of the amino acid sequence according to SEQ ID NO: 9 (VH3) and the VL domain comprises or consists of the amino acid sequence according to SEQ ID NO: 16 (Vκ4);

e) wherein said VH domain comprises or consists of the amino acid sequence according to SEQ ID NO: 10 (VH4) and the VL domain comprises or consists of the amino acid sequence according to SEQ ID NO: 13 (Vκ1);

f) wherein said VH domain comprises or consists of the amino acid sequence according to SEQ ID NO: 10 (VH4) and the VL domain comprises or consists of the amino acid sequence according to SEQ ID NO: 14 (Vκ2);

g) wherein said VH domain comprises or consists of the amino acid sequence according to SEQ ID NO: 10 (VH4) and the VL domain comprises or consists of the amino acid sequence according to SEQ ID NO: 15 (Vκ3);

h) wherein said VH domain comprises or consists of the amino acid sequence according to SEQ ID NO: 10 (VH4) and the VL domain comprises or consists of the amino acid sequence according to SEQ ID NO: 16 (Vκ4);

i) wherein said VH domain comprises or consists of the amino acid sequence according to SEQ ID NO: 11 (VH5) and the VL domain comprises or consists of the amino acid sequence according to SEQ ID NO: 13 (Vκ1);

j) wherein said VH domain comprises or consists of the amino acid sequence according to SEQ ID NO: 11 (VH5) and the VL domain comprises or consists of the amino acid sequence according to SEQ ID NO: 14 (Vκ2);

k) wherein said VH domain comprises or consists of the amino acid sequence according to SEQ ID NO: 11 (VH5) and the VL domain comprises or consists of the amino acid sequence according to SEQ ID NO: 15 (Vκ3); or l) wherein said VH domain comprises or consists of the amino acid sequence according to SEQ ID NO: 11 (VH5) and the VL domain comprises or consists of the amino acid sequence according to SEQ ID NO: 16 (Vκ4).

2. The antibody or an antigen-binding fragment thereof according to claim 1, wherein said antibody or said antigen-binding fragment thereof comprises:

a) a VH domain comprising, essentially consisting of, or consisting of the amino acid sequence according to SEQ ID NO: 10 (VH4) and a VL domain comprising, essentially consisting of, or consisting of the amino acid sequence according to SEQ ID NO: 16 (Vκ4), or b) a VH domain comprising, essentially consisting of, or consisting of the amino acid sequence according to SEQ ID NO: 11 (VH5) and a VL domain comprising, essentially consisting of, or consisting of the amino acid sequence according to SEQ ID NO: 15 (Vκ3).

3. The antibody or the antigen-binding fragment thereof according to claim 1, wherein the antibody is a humanized antibody.

4. The antibody or an antigen-binding fragment thereof according to claim 1, further comprising a constant domain, wherein said constant domain comprises, essentially consists of, or consists of the amino acid sequence according to SEQ ID NO: 19 (IgG4 WT constant), wherein said amino acid sequence according to SEQ ID NO: 19 optionally comprises one or more of the following amino acid exchanges:

an amino acid exchange S108P;

the amino acid exchanges T130Q and M308L; and/or the amino acid exchanges M132Y, S134T, and T136E.

5. The antibody or an antigen-binding fragment thereof according to claim 1, wherein the antigen-binding fragment of an antibody is selected from the group consisting of Fab fragments, Fab' fragments, F(ab')$_2$ fragments, Fd fragments, Fv fragments, disulfide-linked Fvs (dsFv), single domain antibodies and single chain Fv (scFv) antibodies.

6. The antibody or an antigen-binding fragment thereof according to claim 1, wherein said antibody or said antigen-binding fragment thereof exhibits one or more of the following properties:

said antibody or said antigen-binding fragment thereof has a binding constant to C5a with a $K_d$ value of 10 nM or less;

said antibody or said antigen-binding fragment thereof exhibits at least 75% blocking activity for biological effects induced by one molecule C5a;

said antibody or said antigen-binding fragment thereof does not inhibit CH50 activity in human plasma; and/or said antibody or said antigen-binding fragment thereof has a reduced immunogenicity as compared to IFX-1.

7. A pharmaceutical composition comprising:

the antibody or an antigen-binding fragment thereof according to claim 3 and one or more pharmaceutically acceptable carriers, diluents, excipients, fillers, binders, lubricants, glidants, disintegrants, adsorbents, and/or preservatives.

8. A method of blocking or inhibiting C5a-stimulated CD11b upregulation on immune cells, the method comprising contacting the cells with the antibody of claim 3, or an antigen-binding fragment thereof, or a pharmaceutically acceptable composition thereof, wherein the antibody, or an antigen binding fragment thereof, blocks or inhibits the C5a-stimulated CD11b upregulation.

9. The method of claim 8, wherein the immune cells are granulocytes or human granulocytes.

* * * * *